United States Patent
Koop et al.

(10) Patent No.: US 12,295,836 B2
(45) Date of Patent: May 13, 2025

(54) PROSTHETIC HEART VALVE COMPRISING A STENT STRUCTURE HAVING A CONICAL-CONVEX INFLOW REGION AND A LINEAR CYLINDRICAL OUTFLOW REGION

(71) Applicant: BIOTRONIK AG, Buelach (CH)

(72) Inventors: Karsten Koop, Rostock (DE); André Hein, Rostock (DE); Paul Goebel, Rostock (DE); Imanol Flores, Rostock (DE); Andreas Hof, Luebeck (DE); Ulrich Sitz, Rostock (DE); Maik Neitzel, Wissmar (DE); Thomas Kuske, Rostock (DE); Max Linde, Rostock (DE); Stephan Rothstock, Berlin (DE); Matteo Astorino, Buelach (CH); Giuseppe Pisani, Buelach (CH)

(73) Assignee: BIOTRONIK AG, Buelach (CH)

( * ) Notice: Subject to any disclaimer, the term of this patent is extended or adjusted under 35 U.S.C. 154(b) by 774 days.

(21) Appl. No.: 17/414,250

(22) PCT Filed: Dec. 19, 2019

(86) PCT No.: PCT/EP2019/086141
§ 371 (c)(1),
(2) Date: Jun. 15, 2021

(87) PCT Pub. No.: WO2020/127616
PCT Pub. Date: Jun. 25, 2020

(65) Prior Publication Data
US 2022/0054260 A1 Feb. 24, 2022

(30) Foreign Application Priority Data

Dec. 20, 2018 (DE) .......................... 102018133133.9
Jun. 12, 2019 (EP) ...................................... 19179715

(51) Int. Cl.
*A61F 2/24* (2006.01)
*A61F 2/915* (2013.01)

(52) U.S. Cl.
CPC .. *A61F 2/2418* (2013.01); *A61F 2002/91525* (2013.01); *A61F 2250/0026* (2013.01); *A61F 2250/0039* (2013.01)

(58) Field of Classification Search
CPC ........ A61F 2/24; A61F 2/2418; A61F 2/2409; A61F 2/2412; A61F 2250/0039;
(Continued)

(56) References Cited

U.S. PATENT DOCUMENTS

| 6,120,534 A | * | 9/2000 | Ruiz ......................... A61F 2/86 |
| | | | 623/1.3 |
| 7,682,390 B2 | * | 3/2010 | Seguin .................. A61F 2/2433 |
| | | | 623/2.14 |

(Continued)

FOREIGN PATENT DOCUMENTS

| EP | 3184082 A1 * | 6/2017 | ........... A61F 2/2418 |
| WO | 2011147849 A1 | 12/2011 | |

OTHER PUBLICATIONS

International Search Report from the corresponding International Patent Application No. PCT/EP2019/086141, dated Jan. 27, 2020.

*Primary Examiner* — Seema Mathew
(74) *Attorney, Agent, or Firm* — Greer, Burns & Crain Ltd.; Steven P. Fallon

(57) ABSTRACT

A vascular implant, in particular a prosthetic heart valve, for providing valve function, has a stent structure with a proximal conical-convex inflow region, a distal, linear cylindrical outflow region, an intermediate transition region, and a corresponding valve arrangement. When the stent structure is in the expanded state, a higher maximum radial force exists in the inlet region in direct comparison to the lower (Continued)

maximum radial force in the outlet region and in the transition region.

17 Claims, 14 Drawing Sheets

(58) Field of Classification Search
CPC .. A61F 2/241; A61F 2/82; A61F 2/246; A61F 2/86; A61F 2/06
See application file for complete search history.

(56) References Cited

U.S. PATENT DOCUMENTS

| | | | |
|---|---|---|---|
| 7,914,569 B2* | 3/2011 | Nguyen | A61F 2/2418 623/2.12 |
| 8,414,645 B2* | 4/2013 | Dwork | A61F 2/2436 623/2.11 |
| 8,652,203 B2* | 2/2014 | Quadri | A61F 2/2418 623/2.11 |
| 9,532,868 B2* | 1/2017 | Braido | A61F 2/2418 |
| 9,913,715 B2* | 3/2018 | Braido | A61F 2/2418 |
| 9,918,833 B2* | 3/2018 | Kovalsky | A61F 2/2418 |
| 10,226,338 B1* | 3/2019 | Rowe | A61F 2/90 |
| 11,234,702 B1* | 2/2022 | Eigler | A61B 5/0215 |
| 2009/0276040 A1* | 11/2009 | Rowe | A61L 27/3625 623/2.18 |
| 2009/0287299 A1* | 11/2009 | Tabor | A61F 2/07 623/1.26 |
| 2010/0049306 A1* | 2/2010 | House | A61F 2/2418 623/1.26 |
| 2010/0049313 A1* | 2/2010 | Alon | A61F 2/2439 623/2.11 |
| 2010/0082094 A1 | 4/2010 | Quadri et al. | |
| 2011/0022149 A1* | 1/2011 | Cox | A61B 17/12177 623/1.11 |
| 2011/0022157 A1* | 1/2011 | Essinger | A61F 2/2436 623/1.11 |
| 2011/0098804 A1* | 4/2011 | Yeung | A61F 2/2412 623/2.1 |
| 2011/0238168 A1* | 9/2011 | Pellegrini | A61F 2/2433 623/2.17 |
| 2012/0078347 A1* | 3/2012 | Braido | A61F 2/915 623/1.26 |
| 2012/0101572 A1* | 4/2012 | Kovalsky | A61F 2/2418 623/2.19 |
| 2012/0271398 A1* | 10/2012 | Essinger | A61F 2/2412 623/1.11 |
| 2013/0030521 A1* | 1/2013 | Nitzan | A61F 2/2412 623/2.13 |
| 2013/0150956 A1 | 6/2013 | Yohanan et al. | |
| 2014/0018906 A1* | 1/2014 | Rafiee | A61F 2/2427 623/1.26 |
| 2014/0214157 A1* | 7/2014 | Bortlein | A61F 2/243 623/2.11 |
| 2014/0249622 A1* | 9/2014 | Carmi | A61F 2/2418 623/2.11 |
| 2014/0350565 A1* | 11/2014 | Yacoby | A61F 2/2418 606/108 |
| 2015/0051693 A1* | 2/2015 | Bertolino | A61F 2/848 623/1.13 |
| 2015/0173898 A1* | 6/2015 | Drasler | A61F 2/2418 623/2.18 |
| 2015/0209140 A1* | 7/2015 | Bell | A61F 2/2418 623/2.18 |
| 2015/0265402 A1* | 9/2015 | Centola | A61F 2/2418 623/2.18 |
| 2015/0272731 A1* | 10/2015 | Racchini | A61F 2/2436 623/2.11 |
| 2015/0272737 A1* | 10/2015 | Dale | A61F 2/2418 623/2.37 |
| 2016/0143733 A1* | 5/2016 | Quadri | A61F 2/2439 623/2.18 |
| 2016/0151153 A1* | 6/2016 | Sandstrom | A61F 2/2418 623/2.18 |
| 2016/0158007 A1* | 6/2016 | Centola | A61F 2/2427 623/2.11 |
| 2017/0049566 A1* | 2/2017 | Zeng | A61F 2/2418 |
| 2019/0053894 A1* | 2/2019 | Levi | A61F 2/2433 |
| 2019/0321171 A1* | 10/2019 | Morriss | A61F 2/2436 |
| 2020/0229956 A1* | 7/2020 | Jackson | A61F 2/848 |
| 2020/0276014 A1* | 9/2020 | Burkart | A61F 2/2418 |
| 2020/0337837 A1* | 10/2020 | Mitra | A61F 2/2433 |
| 2021/0052379 A1* | 2/2021 | Zhao | A61F 2/2427 |
| 2021/0267755 A1* | 9/2021 | Wallace | A61F 2/2409 |
| 2022/0054260 A1* | 2/2022 | Koop | A61F 2/2418 |
| 2022/0104956 A1* | 4/2022 | Pham | A61F 2/958 |
| 2022/0151775 A1* | 5/2022 | Kiss | A61F 2/2418 |
| 2022/0183831 A1* | 6/2022 | Burkart | A61F 2/2418 |
| 2022/0257372 A1* | 8/2022 | Einhellig | A61F 2/2418 |
| 2022/0296367 A1* | 9/2022 | Hoang | A61F 2/2433 |
| 2023/0014100 A1* | 1/2023 | Quadri | A61F 2/2415 |
| 2023/0125281 A1* | 4/2023 | Alleleyn | A61F 2/9525 623/1.11 |
| 2023/0218390 A1* | 7/2023 | Pisani | A61F 2/2418 623/2.18 |
| 2023/0277307 A1* | 9/2023 | Noe | A61F 2/2439 623/2.18 |
| 2023/0285133 A1* | 9/2023 | Eigler | A61F 2/2412 |
| 2024/0024101 A1* | 1/2024 | Levi | A61F 2/2418 |
| 2024/0108463 A1* | 4/2024 | Floersch | A61F 2/2418 |
| 2024/0115377 A1* | 4/2024 | Kibria | A61F 2/2418 |
| 2024/0130856 A1* | 4/2024 | Gong | A61F 2/2418 |
| 2024/0173127 A1* | 5/2024 | Clapp | A61F 2/2436 |
| 2024/0285401 A1* | 8/2024 | Levi | A61F 2/2433 |
| 2024/0325142 A1* | 10/2024 | Vidlund | A61F 2/2412 |
| 2024/0390139 A1* | 11/2024 | Hummel | A61F 2/2418 |
| 2024/0415639 A1* | 12/2024 | Guan | A61F 2/2418 |

* cited by examiner

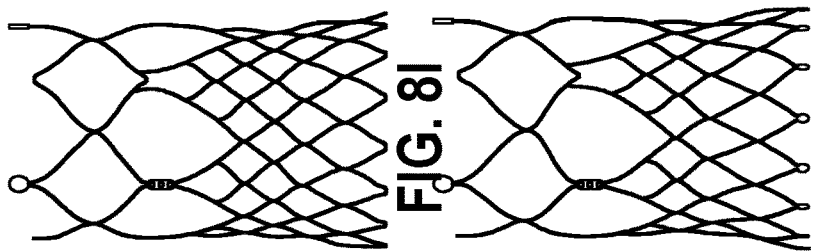
FIG. 8H  15 / 6 cell design
FIG. 8I
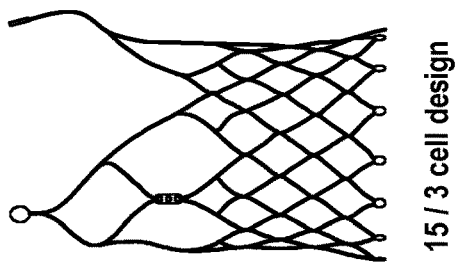
FIG. 8G  15 / 6 cell design
FIG. 8D  15 / 3 cell design
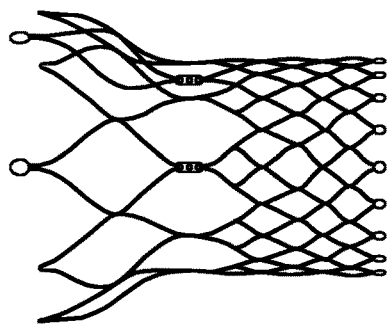
FIG. 8F  15 / 6 cell design
FIG. 8C  18 / 9 cell design
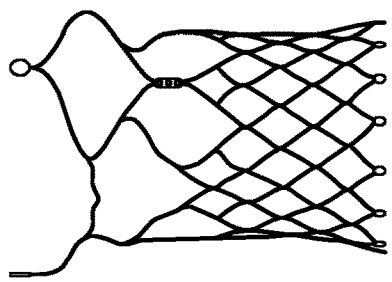
FIG. 8B  15 / 3 cell design
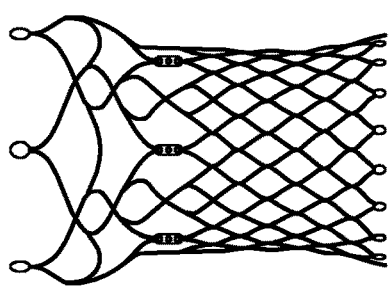
FIG. 8A  18 / 3 cell design
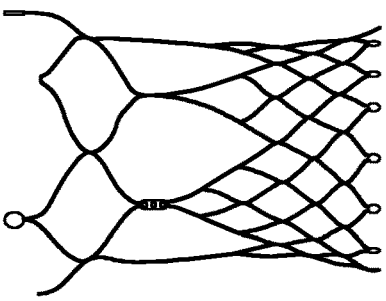
FIG. 8E  15 / 6 cell design 18/9 cell design 18/9 cell design 18/6 cell design

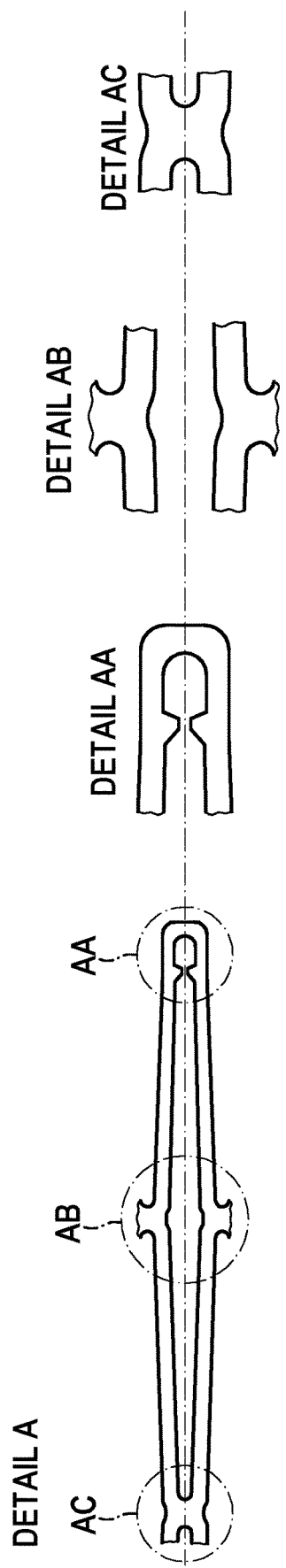
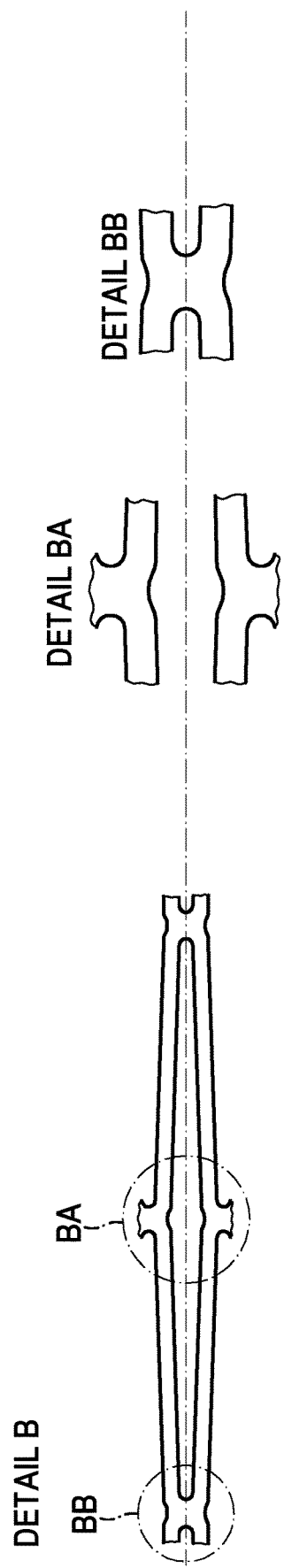

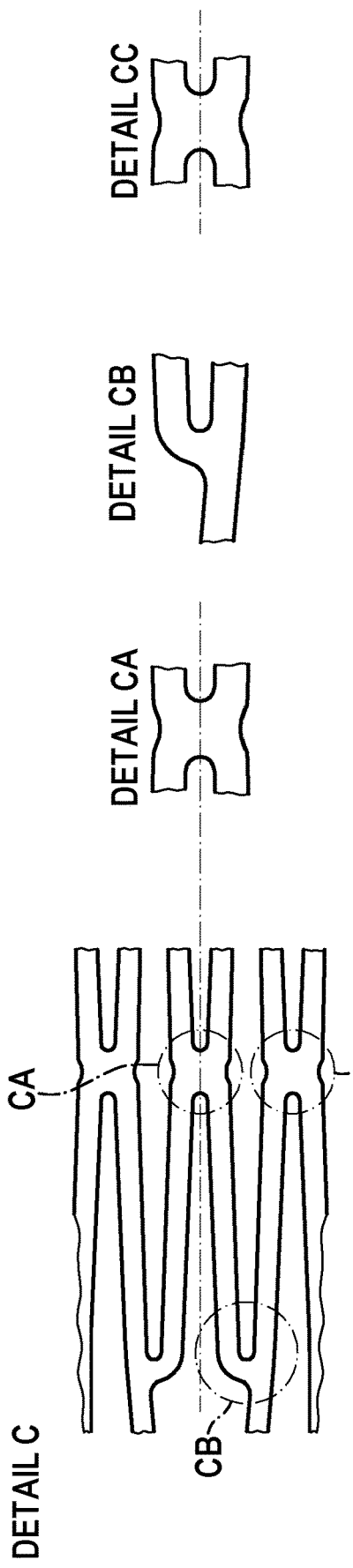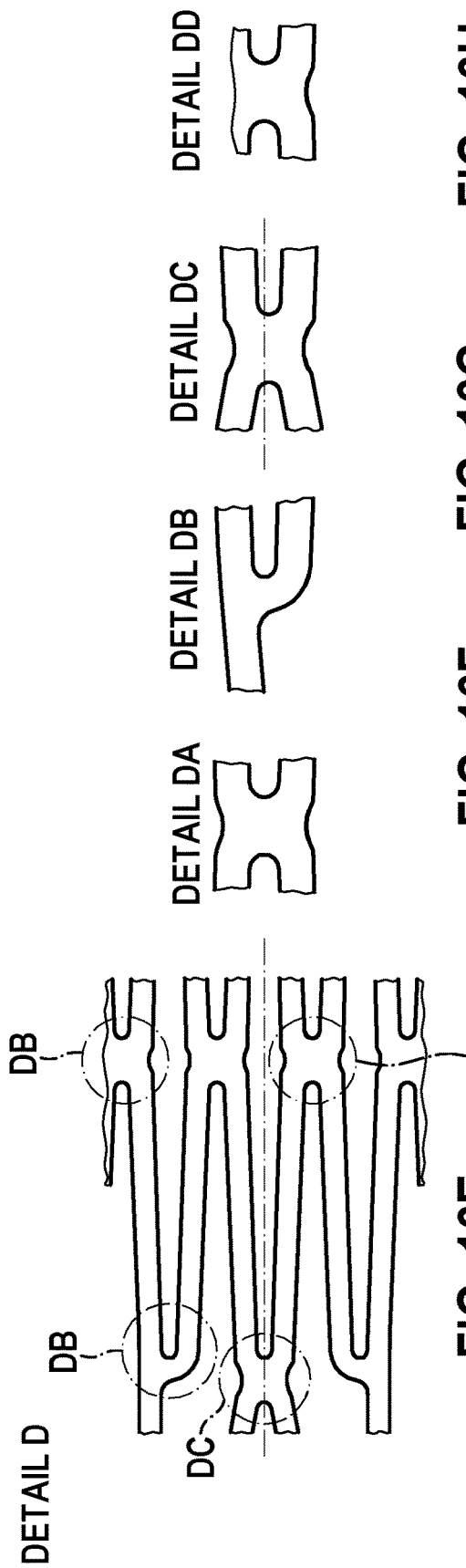

DETAIL E

DETAIL F   FA

DETAIL FA

DETAIL G

PROSTHETIC HEART VALVE COMPRISING A STENT STRUCTURE HAVING A CONICAL-CONVEX INFLOW REGION AND A LINEAR CYLINDRICAL OUTFLOW REGION

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2019/086141, which was filed Dec. 19, 2019, which application claimed priority from European Application Serial Number 19179715.8, which was filed Jun. 12, 2019 and from German Application Serial Number 10 2018 133133.9, which was filed Dec. 20, 2018.

FIELD OF THE INVENTION

The present invention is in the field of prosthetic heart valves, in particular stent-based prosthetic aortic valves, and relates inter alia to methods for their use.

The present invention thus relates to a vascular implant, in particular a prosthetic heart valve, for providing valve function, comprising a stent structure having a conical-convex inflow region, a linear cylindrical outflow region, a transition region, and a corresponding valve arrangement. The invention relates in particular to a prosthetic heart valve comprising a stent structure and valve arrangement according to claim 1. The invention furthermore relates to methods for using the prosthetic heart valve prosthesis according to the embodiment 28. Additional embodiments may be found in this description and in each of the dependent claims.

BACKGROUND

A heart valve operation is used to repair or replace diseased heart valves. A conventional heart valve operation involves a procedure conducted on the open heart and takes place under general anesthesia. For this, in general an incision is made through the patient's sternum (so-called sternotomy), and the patient's heart function is stopped for the period of the intervention, blood being circulated using a heart-lung bypass machine during this period.

The conventional heart valve operation described above may be indicated if the natural heart valve narrows or is narrowed during the systole, which is generally called stenosis, or if the natural valve closes only incompletely during the diastole (insufficiency), so that there is a reverse flow into the ventricle. If the valve is replaced, the native valve is excised and replaced with a biological or mechanical valve.

Mechanical valves require anticoagulant medication for life to prevent the formation of blood clots. In addition, they are characterized by acoustic clicking by the artificial valve that can typically be heard through the chest cavity.

Biological tissue valves typically do not require such medication. Tissue valves may be obtained, for example, from human cadavers (homologous valve) or may be harvested from pigs or cows (xenogeneic heart valves); in addition, they are normally attached to artificial anchoring structures (e.g. a ring) that are then anchored to the patient's heart.

Conventional heart valve surgeries are highly invasive operations involving significant associated risks. Among these risks are hemorrhages, infections, stroke, cardiac infarction, arrhythmia, renal failure, side effects from the anesthesia, and sudden death. Two to five percent of patients die during the surgery.

After surgery, patients may be temporarily more or less seriously limited due to emboli and other factors associated with the heart-lung machine. The first two to three days following the operation are normally passed in an intensive care unit, where cardiac function can be closely monitored.

In order to address the aforementioned drawbacks, due to advances in minimally invasive surgery and in interventional cardiology, in the past 20 years researchers have been encouraged to pursue percutaneous aortic valve replacement. For example, Percutaneous Valve Technologies ("PVT"), in Fort Lee, New Jersey, now Edwards Life-sciences, developed a balloon-expandable stent in which a bioprosthetic valve is integrated. This valve prosthesis is set in the region of the native valve, the native valve being pressed to the side by the stent and the artificial valve thus immediately assuming the valve function. In doing so, the stent, expanded by the balloon, anchors and seals the valve prosthesis. This device from PVT is designed to be implanted in a cardiac catheter laboratory under local anesthesia and using fluoroscopic guidance, so that general anesthesia and open-heart surgery can be avoided. Said device was implanted in a patient for the first time in April 2002.

The valve prosthesis from PVT has a number of drawbacks, however.

Use of the PVT stent is not reversible and the stent cannot be repositioned. This is a critical disadvantage, since incorrect positioning can block the patient's coronary arteries or lead to leaks in the valve all the way to complete migration of the valve.

Another drawback to the PVT device described in the foregoing is its relatively large cross-sectional profile. This valve prosthesis is mounted on a balloon catheter, which renders implantation through the aorta (trans-aortic implantation) difficult. Therefore, a transseptal approach, which requires puncturing the septum, may be necessary for this device in certain circumstances, and this significantly increases the risks of the procedure.

Other artificial replacement heart valves from the prior art use self-expanding stents as carrier structures for attaching, supporting, and anchoring the valve. In the case of endo-vascular aortic valve replacement procedures, precise setting of the aortic valve relative to the coronary arteries and mitral valve is critical. Standard self-expanding systems suffer from low implementation precision, however. The proximal end of the stent is frequently not appropriately released from the catheter system in the first approach, which renders precise and secure setting more difficult and may make necessary, for example, more intensive fluoroscopic exposure in order to be able to undertake precise repositioning. For the aforesaid reasons there are often discrepancies in where the precise inflow and outflow regions of the stent are disposed relative to the native valve, the coronary arteries, and the mitral valve.

Another drawback of previously known self-expanding heart valve systems from the prior art is the lack of radial stiffness and the radial force, which therefore does not build up enough, relative to the surrounding anatomy; this is particularly true in the annular region (Anulus aortae) of the native aortic valve and in the outflow region of the stent.

So that self-expanding stent systems may be advanced easily to the target location via a delivery catheter, it must be possible to compress (crimp) the metal towards the catheter diameter without the metal permanently deforming plastically and losing some of its desired and required radial force (so-called shape memory material—for example, nitinol). This must be assured in particular for multiple compressions (crimping), as normally occurs during repositioning of a valve prosthesis.

At present, known medically applicable alloys for self-expanding stents, such as nitinol, exhibit both lasting plastic deformation and a decrease in material strength (so-called cyclical fatigue) following multiple compressions (crimping), depending on the severity of the deformation. Both of these phenomena lead to a loss in the radial strength of the stent as a support structure for an artificial valve, for example an aortic valve, which then jeopardizes a secure seat for the stent in the surrounding anatomy. This may lead to undesired paravalvular leakage and thus to defective valvular function of the prosthetic heart valve.

If an artificial heart valve is attached in the stent, as is the case for aortic valve replacement (for example, in so-called TAVI or TAVR systems), the stent structure and thus also the valve attached thereto is significantly mechanically limited and challenged in the region of the vessel walls during the diastole. The force for holding back arterial pressure and preventing blood from returning to the ventricle during the diastole is transmitted directly onto the interface between stent and vascular wall. Therefore, the radial force required to keep the expanding stent for the artificial valve in contact with the vascular wall, and not to let it slip away, is much higher than for conventional stents (for example, stents for coronary blood vessels) that do not have valves in them.

Moreover, a self-expanding stent—without sufficient radial force—is limited in its function, is not tight against leaks, and may possibly migrate entirely.

U.S. patent application 2002/0151970, by Garrison et al., describes a two-part device for replacing the aortic valve and suitable for positioning through the aorta of a patient. According to this application, a stent is percutaneously placed over the native aortic valve, and then an artificial valve is positioned in the lumen of the stent. Due to this separation of the stent and valve portion during positioning, the profile of the catheter for the device may be reduced enough to permit positioning via the aorta (trans-aortic positioning) without requiring transseptal access. Both the stent and the artificial valve may be balloon-expandable or self-expanding.

The devices described in the Garrison patent application do use a trans-aortic approach for positioning, but nevertheless suffer from a number of drawbacks.

Initially only the stent part of the device is implanted in a single step and as a single piece in the region of the native valve. Since the valve structure is not implanted into the already set stent until a later step, positioning of the stent—without valve—cannot be functionally evaluated. Any initial incorrect positioning or undesired shortening or migration of the stent during its expansion may lead to incorrect final alignment of the entire valve device.

Other drawbacks of the previously known stent structure, in particular stent structures for aortic valve prostheses, may be summarized as follows:

It is known that excessive radial forces in a stent structure can cause conduction problems that may themselves make necessary additional use of a cardiac pacemaker. On the other hand, in conventional stent structures, the radial forces decrease sharply following multiple repositionings and are thus not adequate for sealing the stent structure against the surrounding anatomy. To counteract this, stent structures from the prior art use external tissue for additional sealing for valve prostheses. However, this leads to larger crimp profiles for the valve prostheses. For this reason, such stent structures must permit smaller crimp diameters, which to date does not seem to have been adequately accomplished. One solution in this regard is a 12 to 6-cell division of the proximal inlet region (12) compared to the distal outlet region (6) of the stent. The greater netting of the cells in the inlet region, with 12 cells, still does not appear to be sufficient for permitting smaller crimping diameters and simultaneously building up adequate radial force for sealing against the anatomy.

With respect to the aforesaid examples of drawbacks of the prior art that are associated with previously known techniques for percutaneous replacement of a heart valve, it is desirable to provide vascular implant devices, in particular a stent-based prosthetic heart valve, that overcome these drawbacks.

More recently, minimally invasive systems and techniques have been developed to facilitate catheter-supported implantation of a valve prosthesis in the beating heart and thus avoid the need for a classical sternotomy and cardio-pulmonary bypass. With transcatheter (or transluminal) techniques, a heart valve prosthesis is sealed in a catheter for insertion and then advanced to the heart, e.g. through an opening in the femoral artery, subclavian artery, aorta, or ventricular apex, in order to gain access to the aortic valve in this manner. The is prosthesis delivered is then set in the so-called "aortic annulus" of the valve to be replaced.

The heart valve prosthesis that is generally used in transcatheter methods includes an expandable, multi-stage frame or stent that supports a valve body having two or more valve leaflets. The actual shape and configuration of a specific prosthetic heart valve is partly a function of the native shape and size of the valve to be repaired (for example, aortic valve, mitral valve, tricuspid valve, or pulmonary valve).

In general, prosthetic heart valves seek to replicate the functions of the valve to be replaced, and the stent used with the prosthesis determines the final size and shape of the valve. Moreover, the stent anchors the transcatheter valve prosthesis in or about the native annulus. One type of transcatheter valve stent frame may initially be provided in an expanded or non-curved state, then may be pressed or compressed about a balloon segment of a catheter. The balloon is then inflated in order to expand and set the prosthetic heart valve. In other supported prosthetic heart valve designs, the stent frame is shaped such that it expands automatically. In these systems, the valve stent is crimped to a desired size and kept in a sleeve in this compressed state for translumenal delivery. Retracting the sleeve from this valve stent permits the stent to expand automatically to a larger diameter and fix at the native valve location. As a rule, conventional suturing of the prosthetic heart valve to the patient's native tissue is not required in either of these types of devices for administering percutaneously compressed heart valves.

In order to achieve long-term anchoring to the native valve location, the stent frame must have and maintain increased strength and resistance to radial forces or pressures. A prosthetic valve that is not anchored to adequately withstand the forces of the continuously varying vascular wall diameter and turbulent circulation there can detach or become ineffective in some other manner (as already described in the foregoing). Moreover, it is desirable to select the size or length of the stent such that increased interaction with the native anatomy is assured. Mesh-like stent structures, for example made of nitinol, have proved quite suitable for satisfying these requirements, and are conventionally configured such that they have a repeating pattern of tightly dimensioned, shaped, and arranged cells. However, it has been found that, following implantation, previous stent-based valve prostheses may lead to the further need for cardiac pacemakers—simply due to issues related to conduction; see above.

Given this background, there is a need for optimizing stent-based prosthetic heart valves that can offer sufficient and secure anchoring in the surrounding anatomy and do not have any effect, or have only a minor effect, on the conducting paths of the heart.

As described in the foregoing, minimally invasive aortic valve replacement is generally used today, even for treating acquired aortic valve stenoses caused by local calcifications. For these types of stenoses, the atrioventricular valves and annulus of a heart are normally more or less highly calcified. These calcifications take the shape of deposits of different hardness that induce geometric changes in the normal anatomy and thus also limit the natural deformability of the tissue structures.

Typically, a purely cylindrical inflow region is placed in the annulus region when an artificial aortic valve is implanted. The valve prosthesis is then sealed in the annulus using the seat of the inflow region. However, if the annulus has an irregular shape due to the aforesaid calcium deposits, generally a gap remains between the valve prosthesis and the annulus if the prosthetic heart valve has cylindrical inflow regions, and this can then lead to paravalvular leakage (so-called leakage loss). Clinical data indicate a clear correlation between survival rate and severity of leakage in a valve prosthesis set in a minimally invasive procedure.

For self-expanding stents that are used as supports and for anchoring a TAVI or TAVR prosthesis, a number of technical properties are essential to ensure post-procedural clinical success.

These properties include:
sufficient radial force for the stent structure for secure anchoring, but without precipitating conduction problems, in particular following multiple repositionings of a TAVI valve or TAVR valve;
free access to the coronary arteries;
stent structure buckling resistance when the TAVI valve or TAVR valve is repositioned and in severely deformed annuli; and,
sufficient sealing tightness for the TAVI valve or TAVR valve.

Another requirement for the functioning of a TAVI valve or TAVR valve is a corresponding outer shape of the implantable prosthesis, the shape fitting the anatomy in question and thus having the required flexibility. In addition, it is advantageous when the geometry of the valve itself does not change at all, or changes only minimally as a function of the available annulus diameter.

The critical property of a TAVI stent or TAVR stent is thus providing an optimum radial force and thus optimum distribution of the radial force longitudinally and around the circumference of the stent structure. The radial force must be of a certain magnitude in order to securely anchor the stent and to assure sealing tightness with respect to the anatomy. On the other hand, the radial force must not be too great, either, because otherwise the heart's conduction system is irritated or it is even possible for tissue damage to occur (see above). Adequate radial force still must always be assured, in particular following multiple repositionings of the stent structure, in which the latter is re-sheathed in a catheter capsule each time. However, nitinol, as a classic stent material, has a cyclical instability that leads to a decrease in the diameter of the stent, and thus to a reduction in the radial force, following each repositioning. Since this effect is a function of the extent of the elongations and the size of the affected region, it is desirable to provide a stent structure, as support structure for a prosthetic heart valve, that minimizes the elongations occurring and maintains an optimum radial force, distributed optimally across the stent structure itself.

Furthermore, even following TAVI implantation or TAVR implantation, the coronary arteries must remain accessible for further interventions by means of a catheter. This applies in particular following a reintervention in which a second prosthesis is set into a prosthesis that has already been implanted (so-called valve-in-valve principle).

In addition, the geometric dimensions of the valve, in particular diameter and height, for optimum functioning as valve (characterized inter alia by complete valve opening, reliable closing of the valve, pressure loss, coaptation, and especially adequate service life) are essential. Therefore, a stent design is to seek to ensure that the geometry of the valve remains the same, to the greatest possible extent, across the permissible diameter range for the annulus. The change in the geometry of the valve between completely expanded stent and implanted configuration should also be as small as possible.

From the literature, it is also known that stent-like structures can collapse inward, either when being re-sheathed in a catheter capsule or when implanted in highly calcified annuli (so-called "buckling" or "infolding"). This buckling or infolding is generally caused by mechanical instability of the stent structure. The prosthesis loses some of its functionality until it fails completely.

For the physiological functioning of a valve prosthesis, a total prosthesis length up to maximally to the transition of the sinus into the ascending aorta is sufficient. On the other hand, the stent structure must have a certain minimum length so that when repositioned the stent is still fixed distally in the catheter capsule on the one side and the prosthesis can deploy proximally such that the valve is already functioning in order to be able to evaluate the functioning of the entire prosthesis prior to complete release.

SUMMARY OF THE INVENTION

A prosthetic heart valve includes a stent structure that is configured to expand from a compressed state for transluminal delivery to a natural expanded state. The stent structure includes a mesh structure that has an essentially tubular shape and that furthermore defines a circumference with contours. The contours define a proximal inlet region, a distal outlet region, and an intermediate transition region. The intermediate transition region connects the inlet region and outlet region to each another, and the mesh structure includes a plurality of closed cells that in the longitudinal direction of the prosthetic heart valve have varying cell sizes and cell configurations to define a plurality of cell patterns that vary in size between the proximal inlet region, the distal outlet region, and the intermediate transition region. A valve arrangement is arranged inside a lumen of the stent structure. The cells in the inlet region are formed and arranged to define a conical-convex outer shape across the entire circumference of the inlet region. The cells in the outlet region are shaped and arranged to define a linear cylindrical outer shape across the entire circumference of the outlet region. Two or more cells in the transition region are shaped and arranged for permitting a cell surface area of suitable size for free access to the coronary arteries. The cells of the inlet region, outlet region, and transition region are configured differently from one another to create, when the stent structure is in the expanded state, a higher maximum radial force in the inlet region in direct comparison to a lower maximum radial force in the outlet region and in the transition region.

BRIEF DESCRIPTION OF THE DRAWINGS

Features, advantages and embodiments of the present invention shall be described hereafter based on the figures. In the drawings:

FIGS. 8A-8I stent structures according to embodiments of the prosthetic heart valve of the present invention that are based on the characteristics of FIG. 1;

FIGS. 15A-15G detail views of a specific mesh structure for stent structure of the prosthetic heart valve of the present invention based on the characteristics of FIG. 1;

FIGS. 16A-16H detail views of a specific mesh structure for stent structure of the prosthetic heart valve of the present invention based on the characteristics of FIG. 1.

DETAILED DESCRIPTION OF THE PREFERRED EMBODIMENTS

Figure 1:
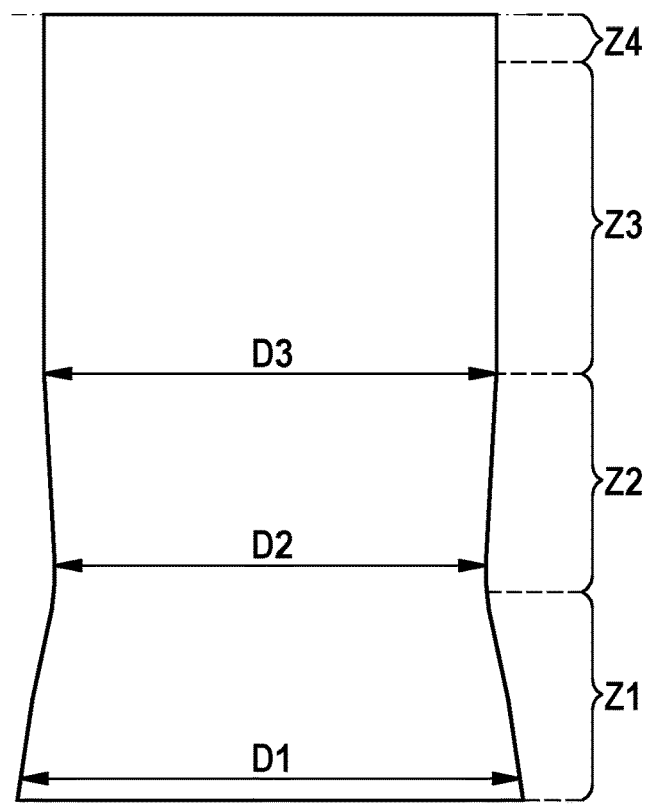
FIG. 1 is a schematic diagram of the outer contours of one embodiment of the prosthetic heart valve of the present invention.

The present disclosure relates primarily to a prosthetic heart valve comprising a stent structure and a valve arrangement. The valve arrangement is arranged inside a lumen of the stent structure. The stent structure is configured such that it may automatically expand from a compressed state for transluminal delivery to a natural, expanded state (self-expanding stent structure). Preferred embodiments provide a novel stent-based prosthetic heart valve that provides a number of advantages. Some advantages include:

a) the reliable sealing tightness of the stent structure of the present invention against the surrounding anatomy, such as, for example, the annulus region of an aortic valve, is assured by a finely netted inlet region that, via its strut and cell design, builds sufficiently high radial force for sealing, and this is even true following multiple repositionings, if there are any, and with a sufficiently small crimp diameter that permits the use of an additional sealing tissue exteriorly on the stent structure in the inlet region (for example, of an outer skirt-shaped element);

b) improved access to the coronary arteries is made possible due to a specially configured transition zone in the stent structure, the transition zone connecting the finely netted inlet region (for example 12, 15, or 18 cells) to a coarsely netted outlet region (for example 3, 6, or 9 cells), and having sufficiently large cells and simultaneously a sharply reduced outlet diameter that prevents complete circumferential or partial circumferential contact between stent outlet and vascular wall of the ascending aorta; thus the outlet region of the present invention and the outlet of the configuration does not have any sealing, anchoring, or aligning function in the stent structure;

c) the geometry of the valve arrangement sutured into the stent structure changes only minimally due to a specially configured outer shape of the stent structure if the diameter of the inlet changes according to the annulus diameter; correspondingly, the geometry of the valve arrangement of the present invention is independent, to the greatest degree possible, of changeable annular diameters;

d) the stent structure is configured in a stable manner such that buckling is prevented in the longitudinal direction of the stent, both when the stent is re-sheathed in a catheter capsule and given severely deformed annuli with significant calcifications;

e) so-called foreshortening of the stent is used intentionally during implantation in order to ensure a sufficiently long stent during positioning of the stent structure so that the valve of the valve prosthesis opens and functioning can be evaluated from outside; when completely released, the stent structure then foreshortens to its final length so that the surrounding anatomy is no longer negatively influenced.

Furthermore, the specially configured outer shape of the stent structure of the present invention permits improved hemodynamics despite intentionally increased radial force distribution.

With reference to FIGS. 1-5 a preferred prosthetic heart valve of the present invention comprises a stent structure that is configured to expand from a compressed state for transluminal delivery to a natural expanded state, the stent structure comprising a mesh structure that has an essentially tubular shape and that furthermore defines a circumference with contours, wherein the contours define a proximal inlet region (Z1), a distal outlet region (Z3), and an intermediate transition region (Z2), wherein the intermediate transition region (Z2) connects the inlet region (Z1) and outlet region (Z3) to one another, and wherein the mesh structure comprises a plurality of closed cells (1, 2, 3) that in the longitudinal direction of the prosthetic heart valve have varying cell sizes (1, 2, 3) and cell configurations (4b), and thus comprises a plurality of cell patterns (1, 2, 3, 4b) that vary in size between the proximal inlet region (Z1), the distal outlet region (Z3), and the intermediate transition region (Z2), and a valve arrangement that is arranged inside a lumen of the stent structure, characterized in that the cells in the inlet region (1) are formed and arranged (5) for defining in the stent structure a conical-convex outer shape across the entire circumference of the inlet region (Z1), and the cells in the outlet region (2) are shaped and arranged for defining in the stent structure a linear cylindrical outer shape across the entire circumference of the outlet region (Z3), and two or more cells in the transition region (3) are shaped and arranged for permitting (3) a cell surface area of suitable size for free access to the coronary arteries, further characterized in that the cells of the inlet region (1), outlet region (2), and transition region (3) are configured differently from one another to always build up, when the stent structure is in the expanded state, a higher maximum radial force in the inlet region (Z1) in direct comparison to the lower maximum radial force in the outlet region (Z3) and in the transition region (Z2).

With this design, the prosthetic heart valve may be set relative to the native anatomy such that the inlet region builds a radial force intentionally elevated compared to the radial force of the outlet region and transition region in order to securely anchor itself in the annulus region, but at the same time the radial force of the inlet region is not increased such that it has a negative effect on the heart's conduction paths or impedes conduction.

Each of the closed cells includes a plurality of struts that are connected to one another.

In some embodiments, a dimension of at least one of the struts of the closed cells in the inlet region is smaller than a corresponding dimension of a corresponding strut of the closed cells in the outlet region. In other embodiments, the inlet region and the outlet region include a node element that connects two struts of each of the closed cells to one another, and one dimension of at least one of the node elements in the inlet region is smaller than a corresponding dimension of each of the node elements in the outlet region.

In this context, the cells in the inlet region are configured to have the highest radial force along the circumference of the inlet region of the stent structure in its natural state than the corresponding cells in the outlet and transition regions.

Still other aspects according to the principles of the present invention relate to a method for treating a patient's native heart valve, for example a patient's aortic valve. The method includes supplying a prosthetic heart valve of the present invention as described herein to the native heart valve, for example to a patient's native aortic valve. In this case, the step for delivering the prosthetic heart valve includes retaining the stent structure in the compressed state inside a delivery device. The prosthetic heart valve is then set by the delivery device, including the stent structure, which expands in the direction of the natural state, into the native heart valve. The inlet region (having the highest radial force) is oriented to a desired anatomical position of the native heart valve, for example the annulus of an aortic valve. In some embodiments, therefore, the native heart valve is an aortic valve, and the desired anatomical position is disposed in the annulus.

The aforesaid object of the invention is attained using the prosthetic heart valve of the present invention, in particular using the included stent structure, as follows:

The present invention relates to vascular implant devices. In particular, the present invention refers to stent-based vascular implants, preferably comprising an artificial heart valve for endovascular or percutaneous replacement of a native heart valve. The invention is directed in particular at an aortic valve prosthesis (TAVI valve or TAVR valve) that can replace a patient's natural aortic valve.

Sufficient sealing of the prosthetic heart valve is also be provided by cells in the inlet region of the stent that are relatively small compared to the rest of the stent, since small cells are better able to adapt to anatomical irregularities in the annulus region, for instance if there are calcifications.

According to the invention, the stent should therefore have larger cells in the outlet region than in the inlet region, the inlet region and outlet region being connected by means of a transition zone made of closed cells in variable size. However, a cell size in this transition zone should have an opening on the stent structure that is sufficient for ensuring access by means of catheter and for providing free access to the coronary arteries. The diameter of the outlet region should be selected such that no functionally relevant contact occurs between the wall of the aorta and the outlet region of the stent structure. That is, the outlet region of the stent structure should be designed to produce no complete circumferential contact to the surrounding anatomy or to produce only partial circumferential contact to the surrounding anatomy, such contact resulting, however, in no functionally relevant contact for the prosthetic valve prosthesis.

The design-dependent shortening of the stent structure during the expansion should therefore be intentionally used for active foreshortening of the stent to the anatomically reasonable length following complete implantation.

In one embodiment, the prosthetic heart valve of the present invention comprises a stent structure as a support structure and a valve arrangement for unidirectional valve function (inlet and outlet direction are oriented only in one direction). In one embodiment of the prosthetic heart valve of the present invention, the valve arrangement is an artificial replacement valve that is attached to the stent structure, preferably an artificial TAVI valve or TAVR valve comprising a plurality of valve leaflets, more preferably three valve leaflets, and a plurality of skirts, more preferably a plurality of skirts within the stent structure (inner skirt) and one or more skirts outside of the stent structure (outer skirt). Even more preferably, three inner skirts are attached to the stent structure and one or more outer skirts are attached to the outside. The stent structure comprises a self-expanding stent, preferably a self-expanding stent structure comprising nitinol.

The valve arrangement (the replacement valve), in particular the TAVI valve or TAVR valve, is designed to be attached inside the stent structure using sutures or adhesive, preferably using sutures at suitable positions on the stent structure, and as such to be released endovascularly in the native aortic region of the patient's heart in order to replace the patient's native aortic valve.

In one embodiment of the invention, the expandable stent structure is produced from a single metal strand, preferably nitinol.

In one embodiment of the invention, the expandable stent structure comprises a convex inflow region.

In one embodiment of the invention, the expandable stent structure comprises a conical-convex inflow region.

In one embodiment of the invention, the expandable stent structure comprises a conical-convex inflow region that extends proximally toward the inlet of the stent structure.

In one embodiment of the invention, the expandable stent structure comprises a linear cylindrical outflow region.

In one embodiment of the invention, the expandable stent structure comprises a linear cylindrical outflow region having a constant diameter.

In one embodiment of the invention, the expandable stent structure comprises a transition region between aforesaid inflow and outflow regions, which transition region connects these to one another.

In one embodiment of the invention, the expandable stent structure comprises a conical transition region between aforesaid inflow region and outflow region, which transition region connects these to one another.

In one embodiment of the invention, the expandable stent structure comprises a tapered transition region between aforesaid inflow region and outflow region, which transition region connects these to one another.

In one embodiment of the invention, the aforesaid transition region comprises one or a plurality of commissure posts, preferably three commissure posts.

In one embodiment of the invention, the aforesaid transition region comprises one or more M-shaped cells.

In one embodiment of the invention, the expandable stent structure comprises one or more connector elements at the distal end of the linear cylindrical outflow region.

In one embodiment of the invention, the expandable stent structure comprises one or more connector elements at the distal end of the linear cylindrical outflow region, the aforesaid connector elements having an eyelet.

In one embodiment of the invention, the expandable stent structure comprises one or more connector elements at the distal end of the linear cylindrical outflow region, which connector element(s) is/are inclined inward toward the center axis of the stent.

In another embodiment of the invention, the aforesaid connector elements have atraumatic apical structures in the distal direction.

In one embodiment of the invention, the expandable stent structure comprises a conical-convex inflow region as described in the foregoing, a linear cylindrical outflow region as described in the foregoing, and a transition region as described in the foregoing that connects the inflow region and the outflow region to one another.

In one embodiment of the invention, the expandable stent structure comprises a conical-convex inflow region as described in the foregoing that expands proximally toward the inlet, a linear cylindrical outflow region as described in the foregoing comprising one or more connector elements at the distal end of the outflow region, and a transition region as described in the foregoing that connects the inflow region and the outflow region to one another.

In one embodiment of the invention, the expandable stent structure comprises a conical-convex inflow region as described in the foregoing that expands proximally toward the inlet, a linear cylindrical outflow region as described in the foregoing comprising one or more, preferably three, distal connector elements, more preferably one or more, preferably three, connector elements inwardly inclined towards the center of the outflow, more preferably one or more, preferably three, inwardly inclined connectors having atraumatic apical structures when the stent is in the expanded state, further comprising a conical transition region that connects the inflow region and the outflow region to one another.

In one embodiment of the invention, the strut width of individual struts or of entire zig-zag rows of the stent structure may vary across the axial length.

In another embodiment of the invention, the strut width of the struts of one or a plurality of zig-zag rows may be wider in the center between two nodes than in the immediate vicinity of the nodes (so-called belly-configuration).

In another embodiment of the invention, the strut width of the struts of one or a plurality of zig-zag rows may be thinner in the center between two nodes than in the immediate vicinity of the nodes (so-called waist-configuration).

In another embodiment of the invention, individual zig-zag rows or all zig-zag rows have a uniform strut length.

In another embodiment of the invention, individual zig-zag rows or all zig-zag rows have a non-uniform strut length.

In one embodiment of the invention, the cells in the transition region have the largest cell surface area of the entire stent structure of the present invention, in particular in the region of the coronary arteries.

The stent structure and the valve arrangement (for example, a TAVI valve or a TAVR valve) of the prosthetic heart valve for the present invention are preferably configured for endovascular positioning and deployment, preferably for transfemoral and/or transaortic positioning and deployment.

The stent structure of the present invention is furthermore suitable for secure and reliable fixation using the conical-convex inflow region at the height of the native aorta annulus of the native aortic valve.

In one embodiment of the invention, the stent structure is designed in the conical-convex inflow region such that the stent structure, regardless of the current annulus diameter, does not significantly affect the valve geometry or function and has radial force that is sufficient for fixing the stent in this region.

In one embodiment of the invention, in its expanded state the stent structure comprises a conical-convex inflow region having a first diameter and a linear cylindrical outlet region having a second diameter, the first diameter of the inflow region being larger than the second diameter.

In one embodiment of the invention, the prosthetic heart valve comprises a stent structure that has a rest configuration, the stent structure comprising a shape-memory material, preferably nitinol, that in the rest configuration is thermoset.

In one embodiment of the invention, the stent structure of the prosthetic heart valve has an intentionally configured mesh structure that leads to controlled shortening of the stent structure during endovascular implantation.

In one embodiment of the invention, the stent structure of the prosthetic heart valve has an intentionally configured mesh structure in the conical-convex inflow region that leads to controlled shortening of the stent structure in the inflow region during endovascular implantation.

In one embodiment of the invention, the stent structure of the prosthetic heart valve has an intentionally configured mesh structure in the linear cylindrical outflow region that leads to controlled shortening of the stent structure in the outflow region during endovascular implantation.

In each of the embodiments of the invention described herein, the mesh structure of the stent structure may be adapted for a controlled foreshortening of the stent structure during implantation.

The valve arrangement of the present invention (for example, a TAVI valve or TAVR valve) of the stent structure of the present invention is disposed inside the stent structure and is designed to admit a blood flow during the systole and to prevent blood from flowing backward during the diastole following deployment (unidirectional blood flow).

In one embodiment of the invention, at least part of the stent structure is covered by a biocompatible film or pericardium, and possibly by an additional element on the inside of the stent structure, which element is configured for reducing paravalvular leakage and regurgitation.

In one embodiment of the invention, at least part of the stent structure is covered by a biocompatible film or pericardium and possibly by an additional element that is configured for reducing paravalvular leakage and regurgitation.

In one embodiment of the invention, at least part of the stent structure is covered by a biocompatible film or pericardium, and possibly by an additional element on the inside of the stent structure, and at least in part is covered by a biocompatible film or pericardium and possibly an additional element on the outside of the stent structure, which element is configured for reducing paravalvular leakage and regurgitation.

Another aspect of the invention provides a prosthetic heart valve of the present invention for endovascular replacement of a patient's heart valve comprising: a customized stent structure according to the invention, and a suitable valve arrangement that fits therewith (for example, a TAVI valve or TAVR valve), wherein the customized stent structure is embodied to form, with the valve arrangement, a composite device that replaces the natural heart valve in an endovascular manner.

In one embodiment of the invention, the stent structure has a conical-convex inflow region (Z1) (so-called annulus zone) that is defined by a first diameter (D1) and a second diameter (D2; "Belly Nadir"), D1 being larger than D2 and the outer surface area of this Z1 region being characterized in that it is curved outward in the longitudinal direction (convex or double curved).

In one embodiment, a simply conical valve zone (Z2; valve zone) connects to the region Z1 with a cone opposing Z1, wherein Z2 is defined by a first diameter (D2), which may be the smallest diameter of the entire prosthetic heart valve, and a second diameter (D3; so-called "Attachment" diameter).

Thus, in one embodiment of the invention, the aforesaid diameter D2 is always smaller than the diameter D3.

In one embodiment of the invention, the zone Z2 connects to a linear cylindrical outflow zone (Z3) (so-called outflow region) that is characterized in that the diameter D3 in the entire zone Z3 is fixed and thus remains the same. This leads to a so-called "linear cylindrical outflow" of the prosthetic heart valve in the present invention.

With the above context, in another embodiment of the invention the expression "linear" is to be understood as "substantially linear" by the person skilled in the art, meaning that slight deviations in diameter along the outflow zone Z3 may occur; however, still resulting in a substantially linear outer shape of said zone Z3.

In one embodiment of the invention, connected to the aforesaid outflow region (Z3) is a connector zone (Z4) that may preferably comprise 3 stent connectors that further preferably may be curved inward by individual strand and further preferably may have atraumatic structures, for example atraumatic tip elements.

Another embodiment of the invention is characterized by a stent structure that has a certain number of cells in the circumferential direction in the inflow region (a), wherein said number of cells is divisible by 3 in order to provide a ⅓ symmetry; furthermore characterized in that another number of cells in the circumferential direction are present in the outflow region (b) and is also divisible by 3, but this number is less than the number of cells in the aforesaid inflow region (a).

In one embodiment of the invention, both regions a) and b) are connected to one another via a so-called transition region c) that provides the connection between inflow region a) and outflow region b).

In one embodiment of the invention, the conical-convex inflow region (a) has 12, 15 or 18 cells (1) and the linear cylindrical outflow region (b) has 3, 6 or 9 cells (2). In this configuration, the connection between inflow region and outflow region may be produced, for example, by 3 attaching elements (4a) and 3 M-shaped connecting elements (4b). In this case each M-shaped connecting element comprises two parallel struts or two struts running at an angle to one another in the direction of the longitudinal axis of the stent and that lead is from the tips of two zig-zags of the lower zig-zag row to the upper zig-zag row such that their connecting points are disposed inside the struts of the first zig-zag row, correspondingly between the tips of the upper zig-zag row.

In the context of the invention, the stent structure having an inflow region and outflow region as described in the foregoing may furthermore be designed such that the foreshortening of the inflow region and outflow region may be influenced independently of one another using the number and/or specific embodiment of the stent element, that is, may be controlled in an intentional manner, so that the length of the stent in these regions may be adjusted during and following implantation such that a desired "foreshortening compensation" is induced in these regions, independently of one another, and/or so that undesired "foreshortening compensation" is minimized.

Correspondingly, in one embodiment of the invention, the stent structure described in the foregoing is provided with a defined and intentionally induced "foreshortening compensation" that may be used to ensure sufficient stent length during release from a catheter shaft so that valve function may be started early during the implantation, and after implantation the stent may be intentionally shortened in order to attain an anatomical fit in the native valve region.

In one embodiment of the invention, the stent structure described in the foregoing is further characterized in that the transition zone c) is designed such that there is one or a plurality of large cells (3) for access to the coronary arteries. Consequently, the cells in the center of this embodiment of a stent structure of the present invention are larger than in the inflow region a) and outflow region b).

In one embodiment of the invention, the stent structure described in the foregoing is furthermore characterized in that 4 to 5 closed zig-zag rows in the inflow region are provided with a strut length adjusted to the entry diameter, wherein the first 2 zig-zag rows have the same length and the third and fourth zig-zag rows, independently thereof, also have an identical length. The length of the first two zig-zag rows is greater than the length of the second two zig-zag rows.

In the context of the present invention, the stent structure described herein is designed such that the struts of the stent are arranged such that the stent structure may be completely re-sheathed in a release capsule of a catheter multiple times. A preferred number of re-sheathings is at least three times, more preferably three times.

In one embodiment of the invention, the struts (5) are characterized in that they have a strut width that may vary along the struts so that the width in the center of the struts is smaller than at the node elements and each strut nevertheless has the same length (so-called waist-configuration).

In one embodiment of the invention, the struts (6) are characterized in that they have a strut width that may vary along the struts so that the width in the center is smaller than at the node elements and each strut nevertheless has the same length, but they are shorter than the length of the struts (5).

In one alternative embodiment, the struts (5) are characterized in that they have a strut width that may vary along the struts so that the width in the center is greater than at the node elements and each strut nevertheless has the same length (so-called belly-configuration).

In one alternative embodiment, the struts (6) are characterized in that they have a strut width that may vary along the struts so that the width in the center is greater than at the node elements and each strut nevertheless has the same length, but they are shorter than the length of the struts (5).

Figure 6:
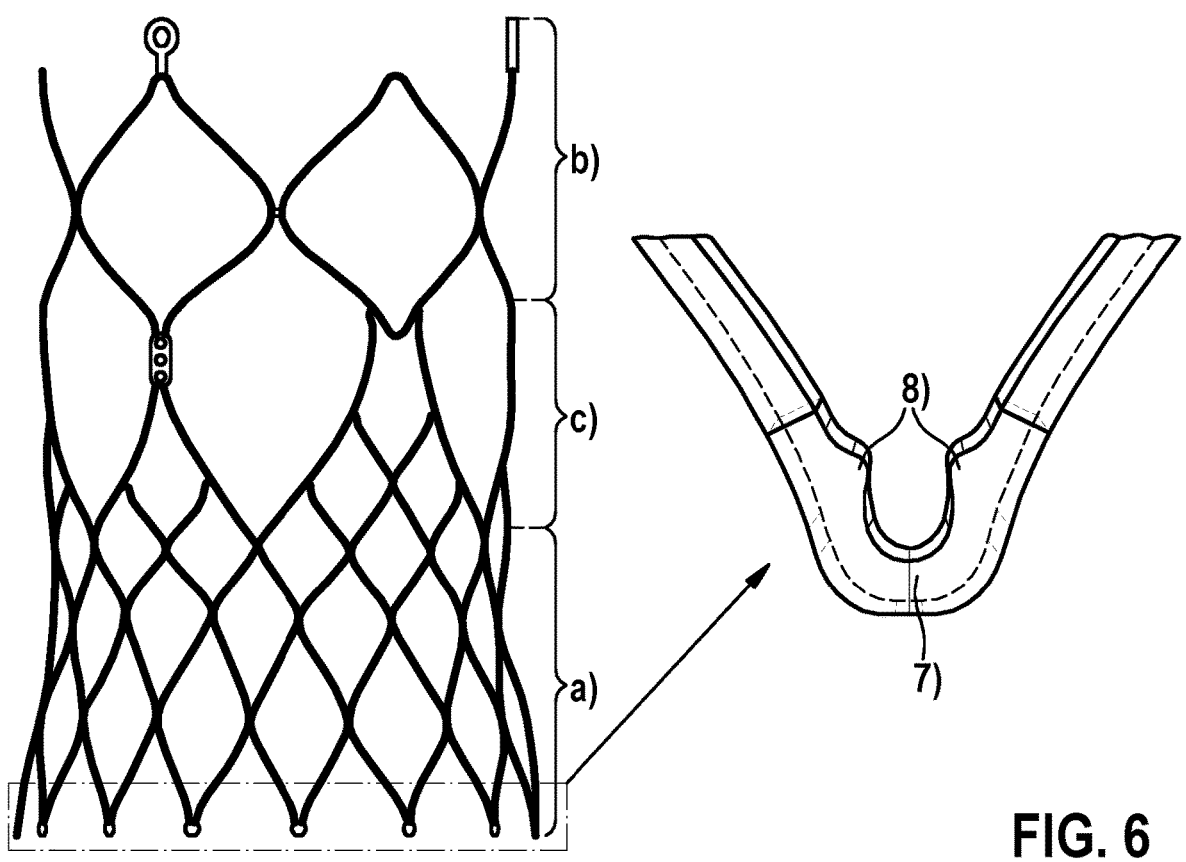
FIG. 6 a stent structure according to one embodiment of the prosthetic heart valve of the present invention with atraumatic tip elements and that is based on the characteristics of FIG. 1.

In one embodiment of the invention in FIG. 6, the stent structure described in the foregoing is characterized in that the struts (5, 6) have a strut width that may vary along the struts so that the width is minimal at two positions (see 6a, for example) along the strut and is the same in a preferred configuration. The strut width (see 6b, for example) between the two positions (6a) is larger but equal to or smaller than the strut width at the nodes (see 6c, for example) (so-called "double waist").

In one embodiment of the invention in FIG. 6, the stent structure described in the foregoing is characterized in that at the inflow edge in the conical-convex inflow region there are atraumatic apical tip elements that are characterized by a simple apical arc (7) having a large radius and 2 individual thickenings in the strut width in the vicinity of the arc (8) that provide a fixed position for the suture nodes disposed at the apical tip of the cells (so-called Nutcracker design).

The stent structure of the present invention has a plurality of technical advantages over the prior art:

The stent structure of the present invention has sufficient and relatively stable radial force that is always highest in the inflow region so that multiple repositionings, preferably three repositionings, —for example of a TAVI valve or TAVR valve based on this stent structure—are possible and the radial force remaining after the repositioning, particularly in the inflow region, is higher than the remaining radial force of comparable valve prostheses from the prior art. At the same time, unimpeded access to the coronary arteries is provided due to the configuration of the stent structure having a finely netted inlet region (corresponds to higher number of cells compared to the outlet region), a coarse mesh outlet region (corresponds to lower number of cells compared to the inlet region), and a transition zone (transition region) disposed therebetween and comprising cells in sufficient size.

In one embodiment of the invention, the aforesaid transition region of the stent structure always comprises the largest cells in relation to the rest of the mesh structure.

Simultaneously, reliable sealing of the prosthesis is attained by using smaller, more finely netted cells in the inlet region, in particular due to the build-up of the highest radial force in the conical-convex inflow region compared to the other parts of the mesh structure of the stent of the present invention.

The ability of the coronary arteries to be reached, mentioned in the foregoing, is even further enhanced by the present design of a linear cylindrical outlet region of the stent structure, since the dimensions of the outlet region of the present invention are selected to not produce any further contact between stent structure and patient's vascular wall. The delivery catheter may thus pass unimpeded.

Due to the high variability in the anatomy of the ascending aorta, when the anatomy is not favorable, such as, for example, if there is an early and sharply infolded aorta, it is not possible to entirely rule out that part of the outlet region of the present invention will touch the vascular wall. However, this is prevented to the greatest possible extent by the presently disclosed configuration of the outlet region.

As a further technical advantage, due to the outer shape of the stent structure of the present invention, a stable valve geometry is defined that changes relatively little in the provided diameter range of the annulus.

Furthermore, avoiding buckling in the stent structure in the longitudinal direction ("infolding") is a critical advantage, both when re-sheathing the stent structure in a catheter capsule and when the stent structure is implanted in highly irregularly shaped annuli and annuli with major calcifications.

Likewise advantageously, the requirement for a shortened implanted stent with the simultaneous requirement for sufficient length of the stent structure for the implantation process is addressed by the present configurations of the stent structure to permit precise positioning during implantation. This is realized in that, due to the specific distribution of different strut lengths and widths, during the implantation process different regions in the stent structure of the present invention shorten in the desired manner or intentionally do not shorten.

Additional advantages of the stent structure of the present invention to be cited are as follows:

The optimized radial force of the stent structure, which is realized by an elongation-optimized design of the struts in the stent structure, makes possible in particular multiple repositionings of the stent structure during an implantation. Surprisingly, it was possible to optimize the elongation behavior using intentional variation and distribution of different strut lengths and strut widths.

Another critical advantage of the invention is increased sealing of the stent structure against the surrounding anatomy, which prevents paravalvular leaks. The sealing tightness of the prosthesis of the present invention, that is, of the stent structure and valve arrangement, is attained using a specially configured cell structure in the inlet region that nevertheless has sufficient build-up of radial force. To connect the finely netted region of the inlet to the coarsely netted outlet, according to the invention a transition zone is defined between inlet region and outlet region of the stent structure and provides free and generous access to the coronary arteries. Correspondingly, the cells in the outlet region are likewise configured with sufficient size.

Consequently, the stent structure of the present invention also ensures access to the prosthesis with a conventional catheter for diagnostic purposes or further implantation of another prosthetic heart valve (valve-in-valve principle).

Another advantage is that possible longitudinal buckling of the stent structure during one or more re-sheathing processes of a prosthesis is avoided due to the design of the stent structure of the present invention. From the literature it is known that various stent designs can tend to buckle inwardly in the longitudinal direction during re-sheathing in a catheter capsule in order, for example, to reposition a valve prosthesis. The same behavior may be found when stents are set in highly calcified or deformed annuli. This undesired behavior is avoided by the aforesaid designs of the inlet region, transition region, and outlet region.

With the aforesaid advantages combined, the present invention provides for the first time a prosthetic heart valve that comprises a stent structure having optimized radial force, improved access to the coronary arteries, and increased stability against infolding when the stent structure is repositioned. These technical advantages are made possible by an intentional arrangement of cells, their intentional definition and distribution of strut lengths and strut widths, and the described outer shaping of the stent structure.

As mentioned herein, the prosthetic heart valve of the present invention may assume a number of different configurations, such as, e.g., a bioprosthetic heart valve having tissue leaflets made of pericardium, a valve having polymer, metal, or tissue leaflets, and may be specially configured for replacing one of the four valves in the human heart, aortic valve replacement being most preferred.

The valve arrangement comprising a valve structure may assume a number of shapes and may be formed, for example, from one or a plurality of biocompatible plastics, synthetic polymers, autograft tissue, homograft tissue, xenograft tissue, or one or a plurality of other suitable materials.

In some embodiments, the valve structure may be formed, for example, from bovine tissue, porcine tissue, equine tissue, ovine tissue, and/or other suitable animal tissue.

In one embodiment, the valve structure may be formed, for example, from kangaroo tissue.

In one embodiment, the valve structure may be formed, for example, from a suitable 3D-printed material.

In some embodiments, the valve structure may be formed, for example, from heart valve tissue, pericardial tissue, and/or other suitable tissue, porcine pericardial tissue being most preferred.

In some embodiments, the valve arrangement may comprise one or a plurality of valve leaflets. Thus, for example, the valve arrangement may be in the form of a bovine or porcine tricuspid pericardial valve, a bicuspid valve, or another suitable valve.

In some designs, the valve arrangement may comprise two or three valve leaflets that are joined at enlarged lateral end regions to create commissure posts, wherein the unbound edges form coaptation edges of the valve arrangement.

In one preferred embodiment, the prosthetic heart valve of the present invention may be configured for replacing or repairing an aortic valve (e.g. with respect to size and shape).

Alternatively, other shapes are provided that follows the specific anatomy of the valve to be repaired (e.g., the prosthetic heart valve of the present invention may be alternatively shaped and/or dimensioned for replacing a native mitral, pulmonary, or tricuspid valve).

The prosthetic heart valve of the present invention may be delivered in different manners to the target heart valve using various transluminal delivery instruments as are known in the prior art. In general, the prosthetic heart valve is compressed in this process and held in an outer delivery device or capsule and then in this compressed state is advanced to the target location before the prosthesis is ultimately released (e.g. by retracting the capsule).

Correspondingly, another aspect of the invention refers to a method for using the prosthetic heart valve, which method is characterized in that it comprises the following steps:

transporting a prosthetic heart valve of the invention to the native heart valve, wherein the step of transporting the prosthetic heart valve includes holding the stent structure in the compressed state inside a delivery device;

supplying the prosthetic heart valve, including the stent structure that automatically expands in the direction of the natural state, to the native heart valve from the delivery device; and, aligning the conical-convex inlet region in a desired anatomical position of the native heart valve.

Although the present disclosure has been described with reference to various embodiments and preferred embodiments thereof, the person skilled in the art will discern that additional changes may be made in shape and details without departing from the original scope of the present disclosure.

Correspondingly, in the context of the present invention all details and embodiments of the prosthetic heart valve may be combined as desired and may be used with the disclosed prosthetic heart valve and with the method for its use. All details and embodiments of the prosthetic heart valve and of the method for its use may likewise be combined as desired and used for any other vascular prosthesis in any desired combination.

Provided there is no indication to the contrary, the general tolerance for the strut width is +/−0.015 mm and for the wall thickness is +/−0.020 mm.

FIG. 1: Schematic depiction of the outer contours of one embodiment of the prosthetic heart valve of the present invention. Z1 designates a conical-convex inflow region (anulus zone) that is defined by a first diameter D1 and a second diameter D2 ("Belly nadir" diameter), D1 being greater than D2, and the outer surface area of this Z1 region being characterized in that it is curved outward in the longitudinal direction (convex or double curved). Connected to the region Z1 is a simple conical valve zone Z2 having a cone opposing Z1, wherein Z2 may be defined by a first diameter D2, which may be the smallest diameter of the entire vascular implant, and a second diameter D3 (so-called "Attachment" diameter), further characterized in that the diameter D2 is smaller than the second diameter D3. Attached to zone Z2 is a cylindrical and thus linear outflow zone Z3 (outflow region) that is characterized in that the first diameter D3 remains the same in the entire zone Z3. This leads to a so-called "linear outflow" for the vascular implant. Finally, a connector zone Z4 is attached. In one embodiment the connector zone may comprise 3 connectors. In another embodiment the connectors, optionally three connectors, may be single-stranded and curved inward and may furthermore have atraumatic tip elements (not shown).

Figure 2:
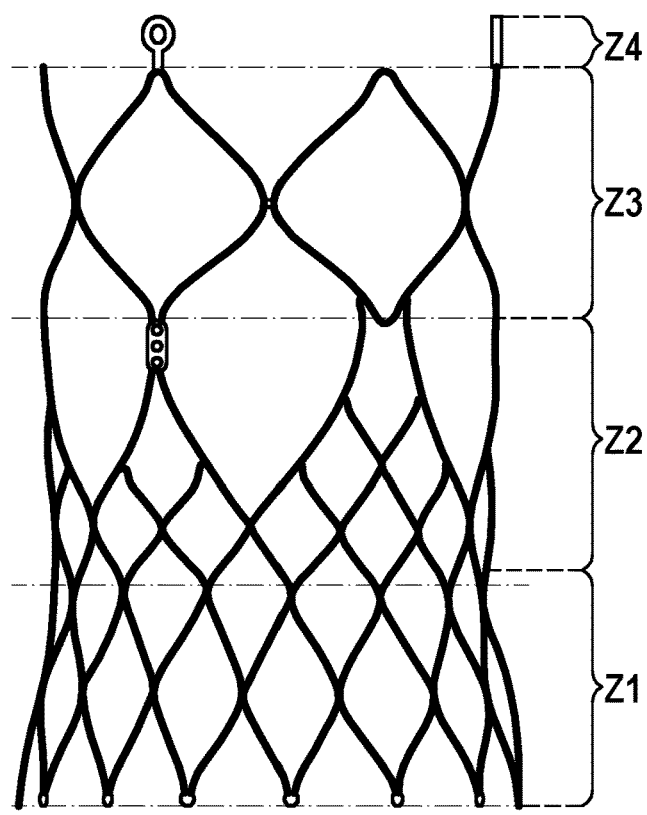
FIG. 2 shows a stent structure according to one embodiment of the prosthetic heart valve of the present invention based on the characteristics of FIG. 1.

FIG. 2: Depiction of a stent structure according to one embodiment of the prosthetic heart valve of the present invention based on the characteristics of FIG. 1. Z1 designates a conical-convex inflow region (annulus zone) that is defined by a first diameter D1 and a second diameter D2 ("Belly nadir" diameter), D1 being larger than D2 and the outer surface area of this Z1 region being characterized in that it is curved outwardly in the longitudinal direction (convex or double curved). Connected to the region Z1 is a simple conical valve zone Z2 having a conical form opposing Z1, wherein Z2 is defined by a first diameter D2, is which may be the smallest diameter of the entire vascular implant, and a second diameter D3 (so-called "Attachment"

diameter), further characterized in that the first diameter D2 is smaller than the second diameter D3. Attached to zone Z2 is a cylindrical and thus linear outflow zone Z3 (outflow region) that is characterized in that the diameter D3 remains the same in the entire zone Z3. This leads to a so-called "linear outflow" for the prosthetic heart valve. The upper limit of the stent structure is a connector zone Z4 that in the embodiment illustrated, by way of example, may comprise 3 connectors. In one embodiment, the connectors, optionally three connectors, may be single-stranded and curved inward and may have atraumatic tip elements (not shown).

Figure 3:
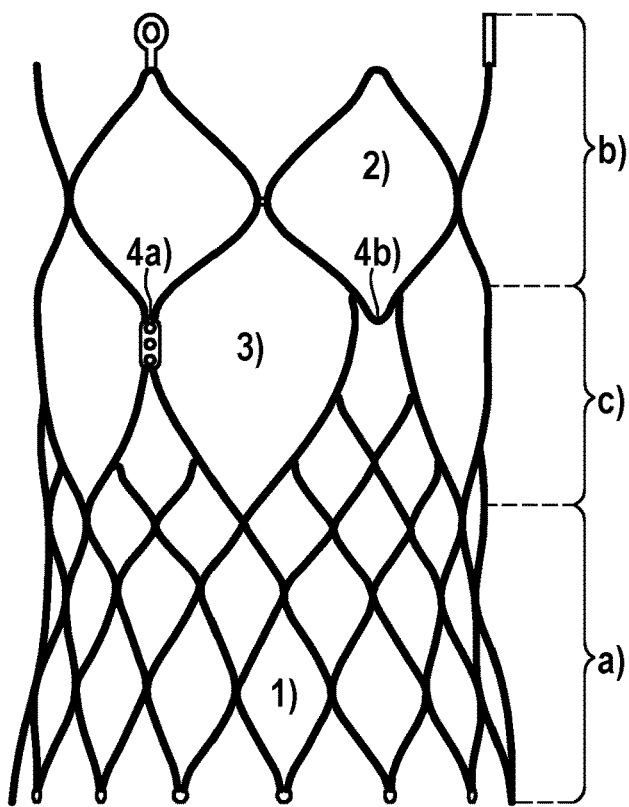
FIG. 3 a stent structure according to one embodiment of the prosthetic heart valve of the present invention with a 1:3 symmetry and that is based on the characteristics of FIG. 1.

FIG. 3: Depiction of a stent structure according to one embodiment of the prosthetic heart valve of the present invention and based on the characteristics of FIG. 1. The embodiment illustrated is characterized by a stent structure that has a certain number of cells in the circumferential direction in the inflow region a), wherein the aforesaid number of cells is divisible by 3 in order to provide a 1:3 symmetry, furthermore characterized in that there are a further number of cells in the circumferential direction in the outflow region b), also divisible by 3, wherein this number is less than the number of cells in the aforesaid inflow region a), however, both regions a) and b) are connected to one another by a so-called transition region c) (transition zone) that connects the inflow region a) and the outflow region b) and in this embodiment comprises the largest cells in the stent structure 3) for free access to the coronary arteries.

In one preferred configuration referring to FIG. 3, the inflow region (1) has 12, 15, or 18 cells and the outflow region (2) has 3, 6, or 9 cells. In this configuration, the connection between inflow region and outflow region may be produced, for example, by 3 attaching elements (4a) and 3 M-shaped connecting elements (4b).

In another preferred configuration referring to FIG. 3 and FIGS. 8 and 9, the inflow region (1) has 12 cells and the outflow region (2) has, optionally, 3, 6, or 9 cells. In another preferred configuration referring to FIG. 3 and FIGS. 8 and 9, the inflow region (1) has 15 cells and the outflow region (2) has, optionally, 3, 6, or 9 cells. In another preferred configuration referring to FIG. 3 and FIGS. 8 and 9, the inflow region (1) has 18 cells and the outflow is region (2) has, optionally, 3, 6, or 9 cells.

In another preferred configuration referring to FIG. 3 and FIGS. 8 and 9, the inflow region (1) has 18 cells and the outflow region (2) has 3 cells. In another preferred configuration referring to FIG. 3 and FIGS. 8 and 9, the inflow region (1) has 18 cells and the outflow region (2) has 9 cells. In another preferred configuration referring to FIG. 3 and FIGS. 8 and 9, the inflow region (1) has 18 cells and the outflow region (2) has 6 cells.

In another preferred configuration referring to FIG. 3 and FIGS. 8 and 9, the inflow region (1) has 15 cells and the outflow region (2) has 3 cells. In another preferred configuration referring to FIG. 3 and FIGS. 8 and 9, the inflow region (1) has 15 cells and the outflow region (2) has 9 cells. In another preferred configuration referring to FIG. 3 and FIGS. 8 and 9, the inflow region (1) has 15 cells and the outflow region (2) has 6 cells.

In another preferred configuration referring to FIG. 3 and FIGS. 8 and 9, the inflow region (1) has 12 cells and the outflow region (2) has 3 cells. In another preferred configuration referring to FIG. 3 and FIGS. 8 and 9, the inflow region (1) has 12 cells and the outflow region (2) has 9 cells. In another preferred configuration referring to FIG. 3 and FIGS. 8 and 9, the inflow region (1) has 12 cells and the outflow region (2) has 6 cells.

In the context of the invention, the stent structure having an inflow region and an outflow region as described in the foregoing for FIG. 3 may furthermore be designed such that the foreshortening of the inflow region and of the outflow region may be influenced independently of one another using the specific embodiment of the stent elements (i.e., using strut width and strut length) so that the length of the stent in these regions may be adjusted during and following implantation to cause a desired Foreshortening Compensation in these regions, independently of one another, and/or to minimize undesired Foreshortening Compensation.

Referring to FIG. 3, this exemplary stent structure is further characterized in that the transition zone c) is designed such that there are one or a plurality of large cells (3), is preferably at least two large cells (3), more preferably at least three large cells (3), for access to the coronary arteries. Consequently, in one embodiment the aforesaid large cells (3) in the transition region may be larger than those in the inflow region and in the outflow region.

Referring to FIG. 3, in one embodiment this exemplary stent structure is further characterized in that 4 to 5 closed zig-zag rows (so-called zig-zags) in the inflow region are provided with a strut length adjusted to the entry diameter, the first 2 zig-zag rows having the same length and the third and fourth zig-zag rows, independently thereof, being of equal length. The length of the first two zig-zag rows is greater than the length of the second two zig-zag rows.

Figure 4:
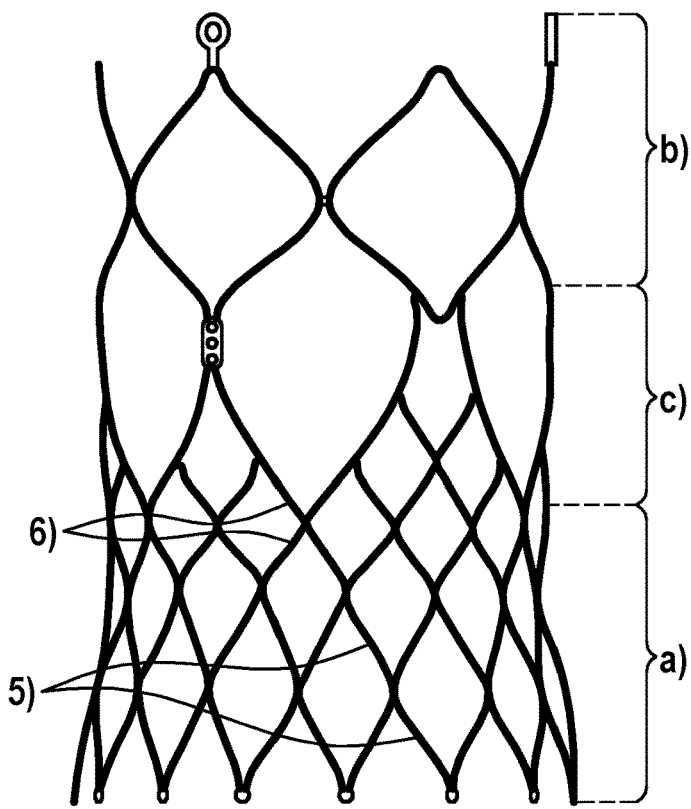
FIG. 4 a stent structure according to one embodiment of the prosthetic heart valve of the present invention that permits early valve function starting and that is based on the characteristics of FIG. 1.

FIG. 4: Depiction of a stent structure according to one embodiment of the prosthetic heart valve of the present invention and based on the characteristics of FIG. 1. FIG. 4 illustrates a stent structure as described in the foregoing having a defined Foreshortening Compensation that may be used for providing sufficient stent length during the release of a catheter shaft so that the valve function may be started early during the implantation, and following implantation the stent may be intentionally shortened in order to attain an anatomical fit in the native valve region.

In the context of the present invention, this stent structure is designed such that the struts for the stent are arranged such that the stent structure may be completely re-sheathed in a release capsule of a catheter. A preferred number of re-sheathing instances is at least three, more preferred is three.

Referring to FIG. 4, the struts (5) are characterized in that they have a strut width that may vary along the struts, so that the width in the center of the struts is smaller than at the node elements and each strut nevertheless has the same length (waist-configuration).

Referring to FIG. 4, the struts (6) are characterized in that they have a width that may vary along the struts, so that the width in the center is smaller than at the node elements and each strut nevertheless has the same length, but this length is shorter than the length of the struts (5).

In one alternative embodiment and referring to FIG. 4, the struts (5) are characterized in that they have a strut width that may vary along the struts, so that the width in the center is greater than at the node elements and each strut nevertheless has the same length (so-called belly-configuration). In one alternative embodiment and referring to FIG. 4, the struts (6) are characterized in that they have a strut width that may vary along the struts, so that the width in the center is greater than at the node elements and each strut nevertheless has the same length, but this length is shorter than the length of the struts (5).

Figure 5:
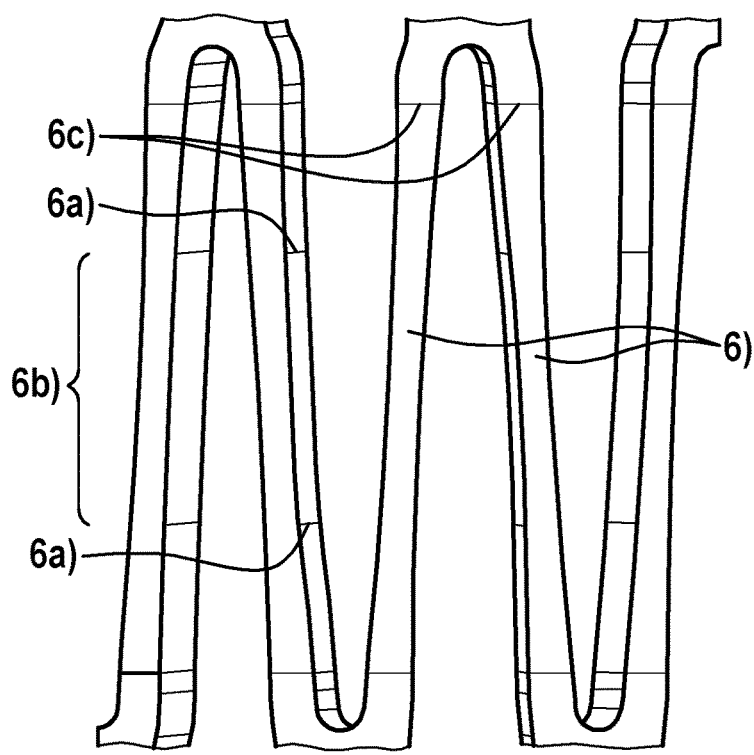
FIG. 5 a stent structure according to one embodiment of the prosthetic heart valve of the present invention with variable strut width and that is based on the characteristics of FIG. 1.

FIG. 5: Referring to FIG. 4, FIG. 5 provides a detailed excerpt from an embodiment of the stent structure of the present invention that is characterized in that the struts (5, 6) have a strut width that may vary along the struts, so that the width at two positions (for example 6a) along the strut is minimal and in one preferred configuration is the same. The strut width (for example 6b) between the two positions (for example 6a) is greater than these but the same as or smaller than the strut width at the nodes (for example 6c) (so-called "double waist").

FIG. 6: Referring to the aforesaid figures, FIG. 6 depicts an embodiment of the stent structure of the present invention that is characterized in that at the inflow edge at the inflow region (see highlighted rectangular section) there are atraumatic tip elements that are characterized by a simple apical arc (7) having a large radius and 2 individual thickenings in the strut width in the vicinity of the arc (8), and the thickenings retaining a fixed position of the suture node disposed at the apical tip of the cells, so-called "Nutcracker design."

Figure 7C:
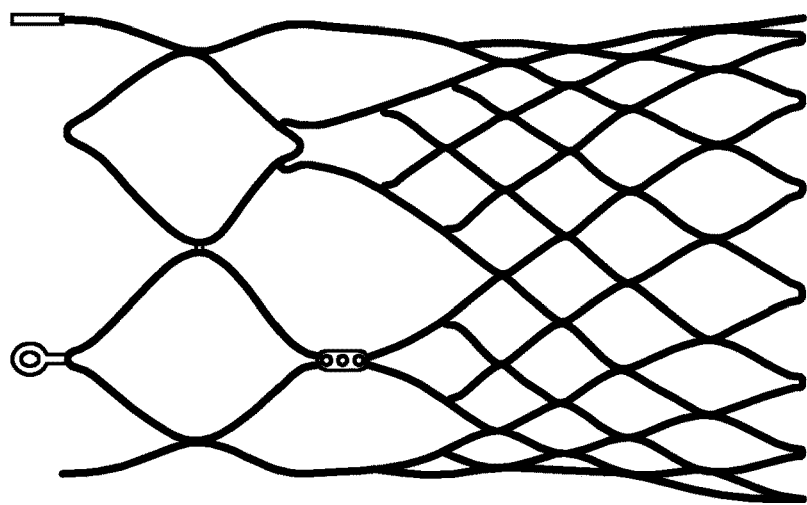
FIGS. 7A-7C stent structures according to embodiments of the prosthetic heart valve of the present invention with zig-zag rows and that are based on the characteristics of FIG. 1.
Figure 7B:
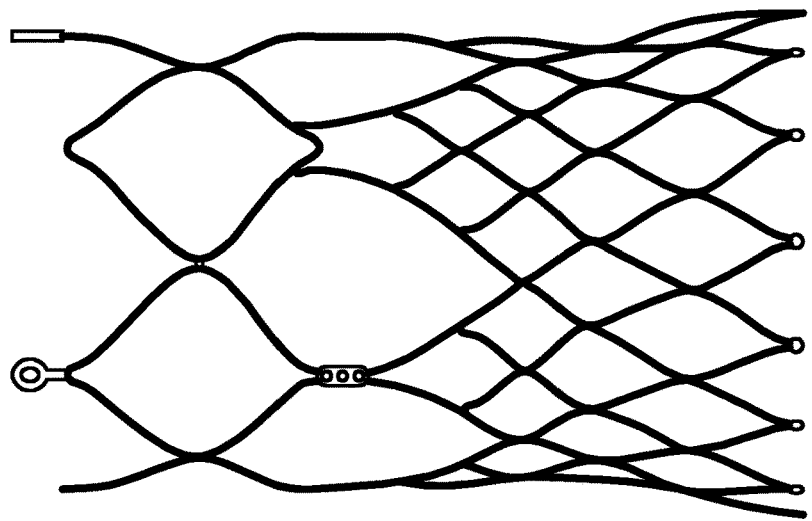
Figure 7A:
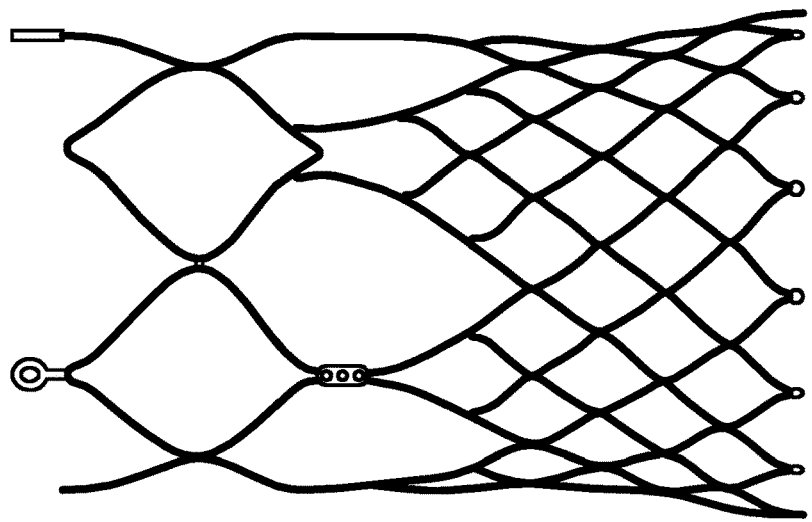

FIGS. 7 through 9: Referring to the aforesaid figures, FIGS. 7 through 9 depict various specific embodiments of the stent structures of the present invention described herein:

FIG. 7A): depicts a stent structure of the present invention that has 5 circumferential zig-zag rows in the conical-convex inlet, in which all struts of these zig-zag rows have the same length.

FIG. 7B): depicts a stent structure of the present invention that has 4 circumferential zig-zag rows in the inlet region, in which stent structure the lower two zig-zag rows have struts that themselves have the same length. The two upper zig-zag rows in the inlet region also have the same strut length as one another, but they are shorter than the strut lengths of the two lower rows.

FIG. 7C): depicts a stent structure of the present invention that has 5 circumferential zig-zag rows in the inlet region, in which stent structure the lower two zig-zag rows have struts that themselves have the same length. The two upper zig-zag rows in the inlet region also have the same strut length as one another, but they are shorter than the strut lengths of the lower two rows. The length of the $5^{th}$ zig-zag row in one embodiment is the same as the length of the struts in the $3^{rd}$ and $4^{th}$ zig-zag rows.

FIGS. 8A-8I: depict specific different embodiments of the stent structure of the present invention having a cell count of 12, 15, or 18 cells circumferentially in the inlet region and a cell count of 3, 6 or 9 circumferential cells in the outlet region. The outlet itself may have closed zig-zag rows or may be open or, in a different embodiment, may be formed by special connectors arranged between the cells. The number of closed zig-zag rows in the inlet is 4 or 5 zig-zag rows.

Figure 9C:
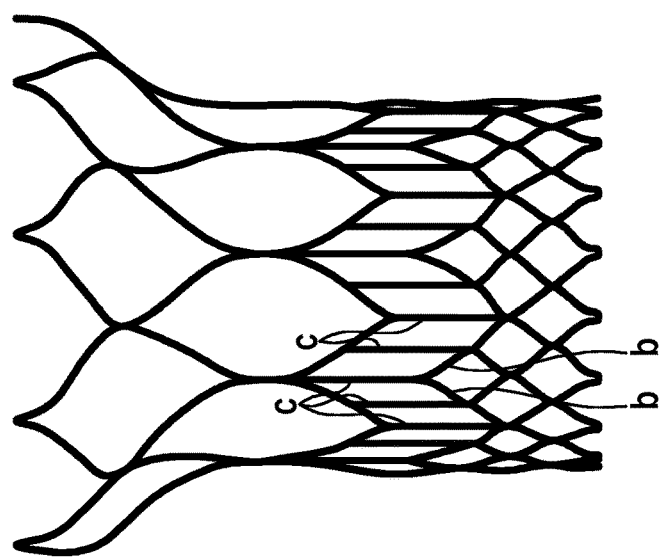
FIGS. 9A-9C stent structures according to embodiments of the prosthetic heart valve of the present invention with alternate transition regions and that are based on the characteristics of FIG. 1.
Figure 9B:
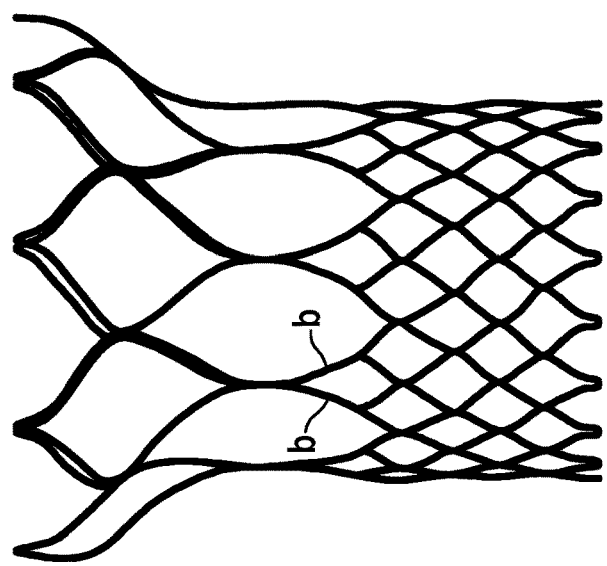
Figure 9A:
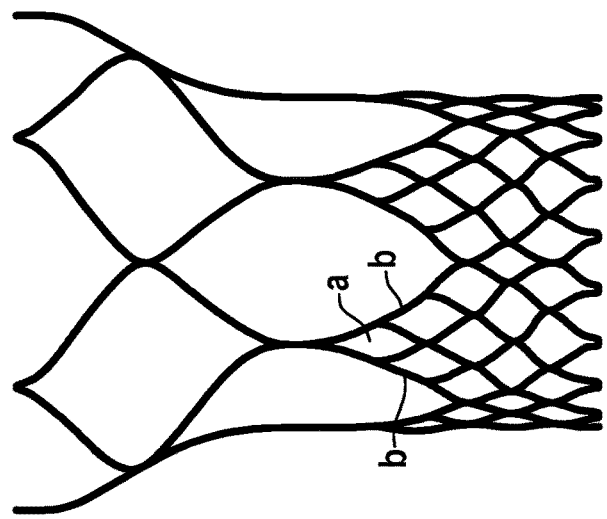

FIGS. 9A-9C: depict specific different embodiments of a transition region (transition zone) of the stent structure of the present invention. This transition region is depicted using 6 additional cells a) and associated struts b) or using only additional struts b) or using additional struts b) and struts c) longitudinally that may vary between 9 and 36 in number.

Figure 10A:
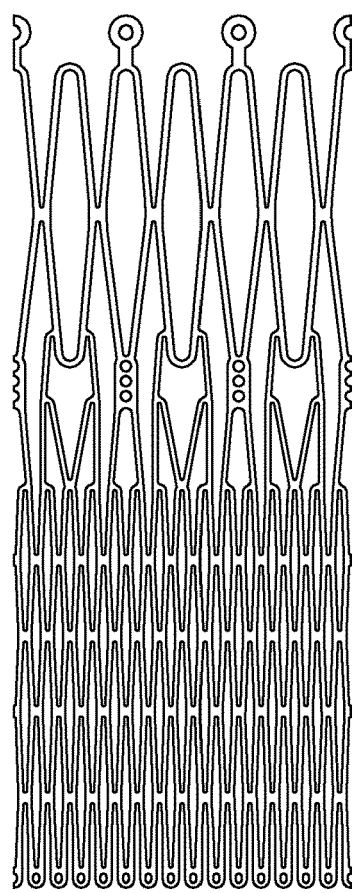
FIGS. 10A-10B a stent according to one embodiment of the prosthetic heart valve of the present invention with 120° symmetry in respective crimped and expanded states and that is based on the characteristics of FIG. 1.

FIG. 10A): depicts by way of example a crimped (compressed) mesh structure for the stent structure of the present invention in 120° symmetry (non-expanded state, following electropolishing; wall thickness=0.515 mm; edge radius >/=0.0175 mm).

Figure 10B:
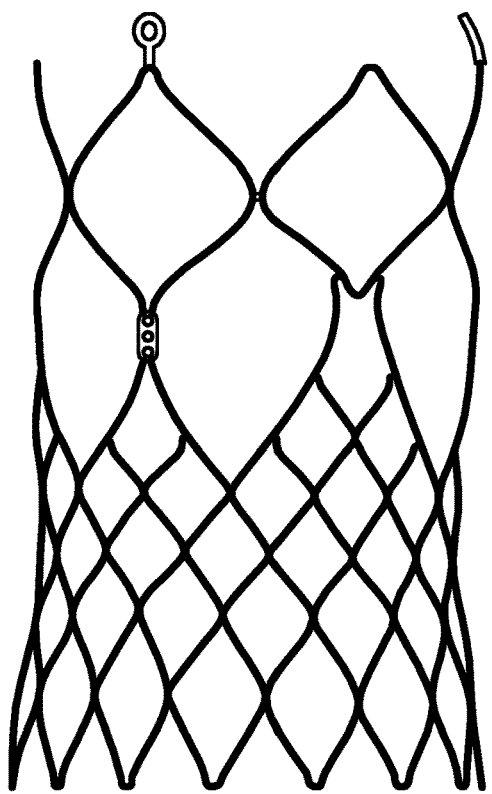

FIG. 10B): depicts by way of example a mesh structure for the stent structure of the present invention in the expanded state having 120° symmetry (following electropolishing; wall is thickness=0.515 mm; edge radius >/=0.0175 mm).

Figure 11A:
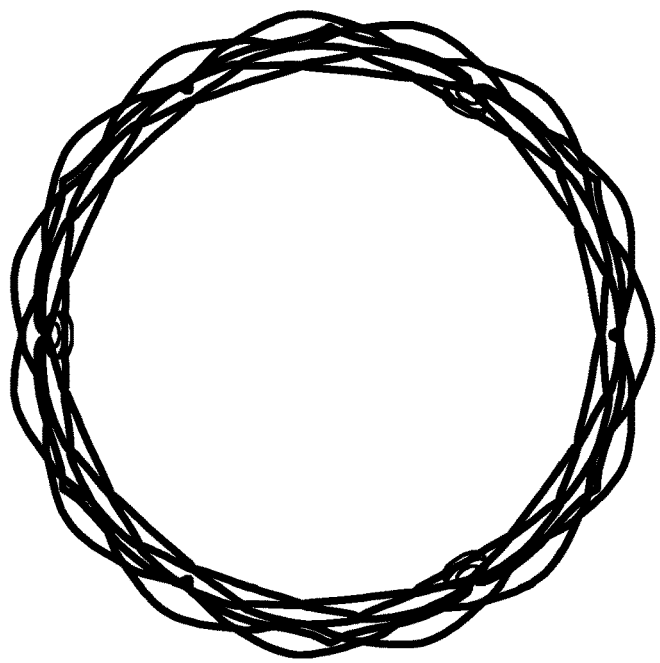
FIGS. 11A-11B top and side views of a specific mesh structure for stent structure of the prosthetic heart valve of the present invention based on the characteristics of FIG. 1.
Figure 11B:
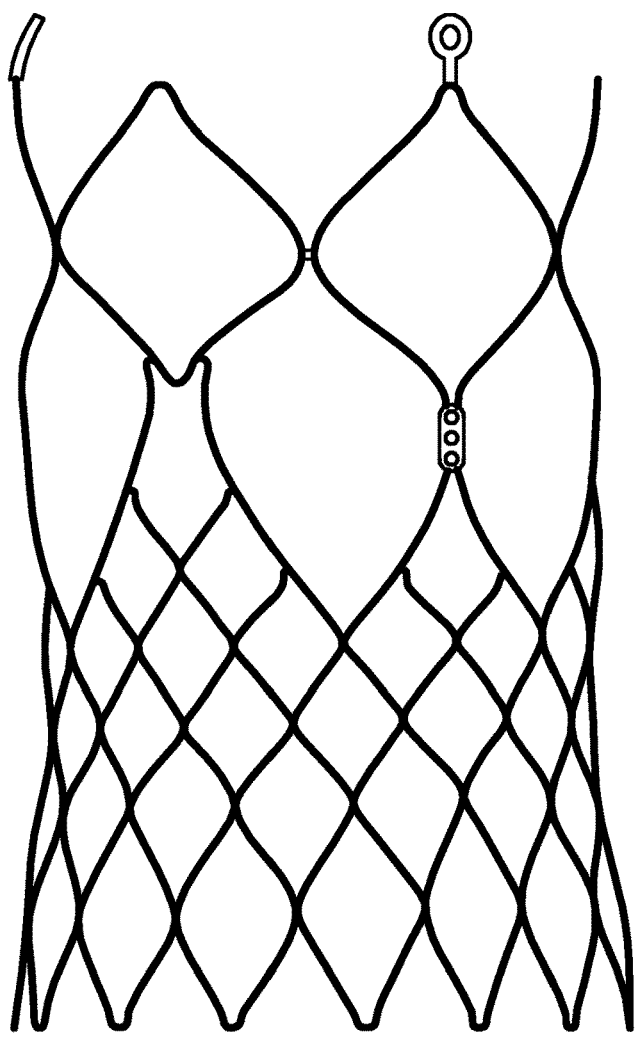

FIGS. 11A-11B: depict by way of example a specific mesh structure for the stent structure of the present invention in the expanded state. FIG. 11A: top view; FIG. 11B: side view.

Figure 12:
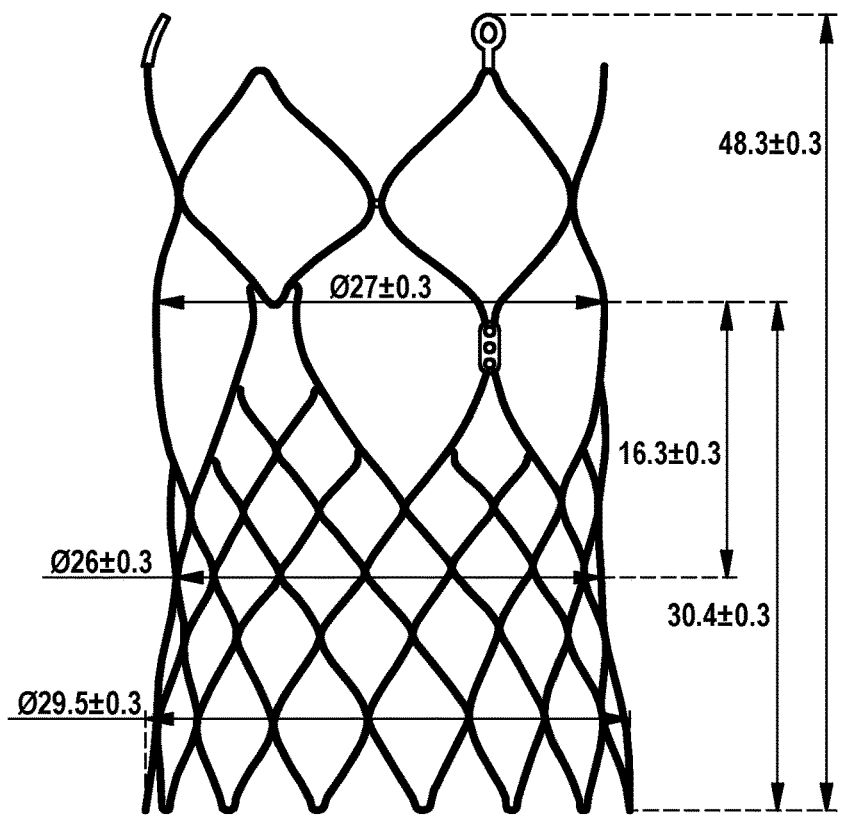
FIG. 12 shows example dimensions for a stent structure in the expanded state according to one embodiment of the prosthetic heart valve of the present invention based on the characteristics of FIG. 1.

FIG. 12: depicts by way of example a mesh structure for the stent structure of the present invention in the expanded state having exemplary dimensions in the context of the invention [in mm].

Figure 13:
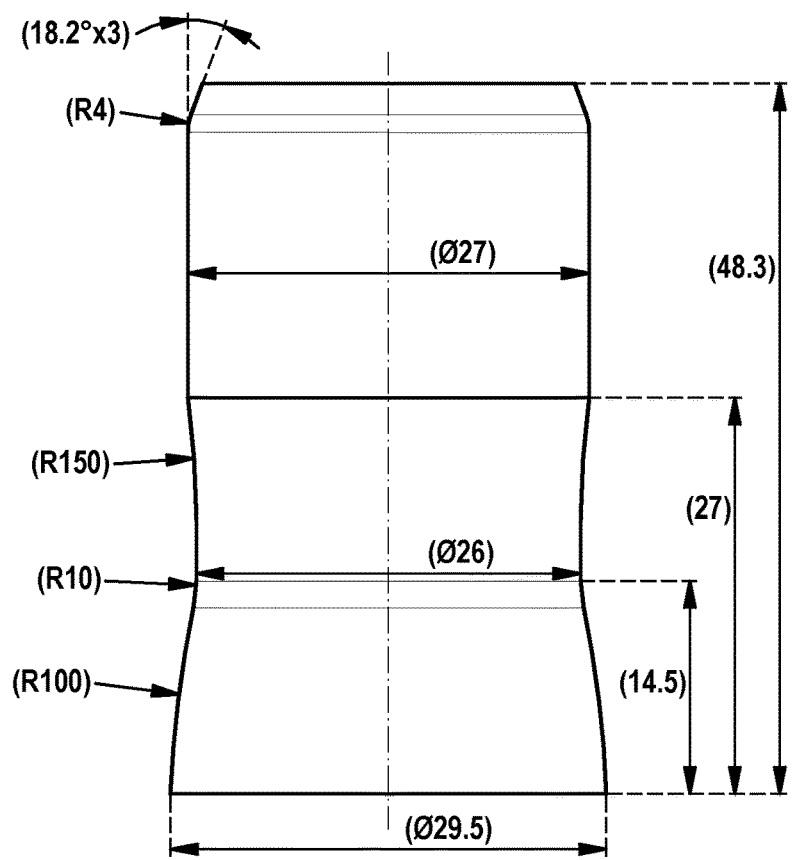
FIG. 13 shows example dimensions and angles for a stent structure in the expanded state according to one embodiment of the prosthetic heart valve of the present invention based on the characteristics of FIG. 1.

FIG. 13: is a schematic illustration of an exemplary outer shape of the stent structure of the present invention in the expanded state with exemplary dimensions [in mm] and angles in the context of the invention.

Figure 14:
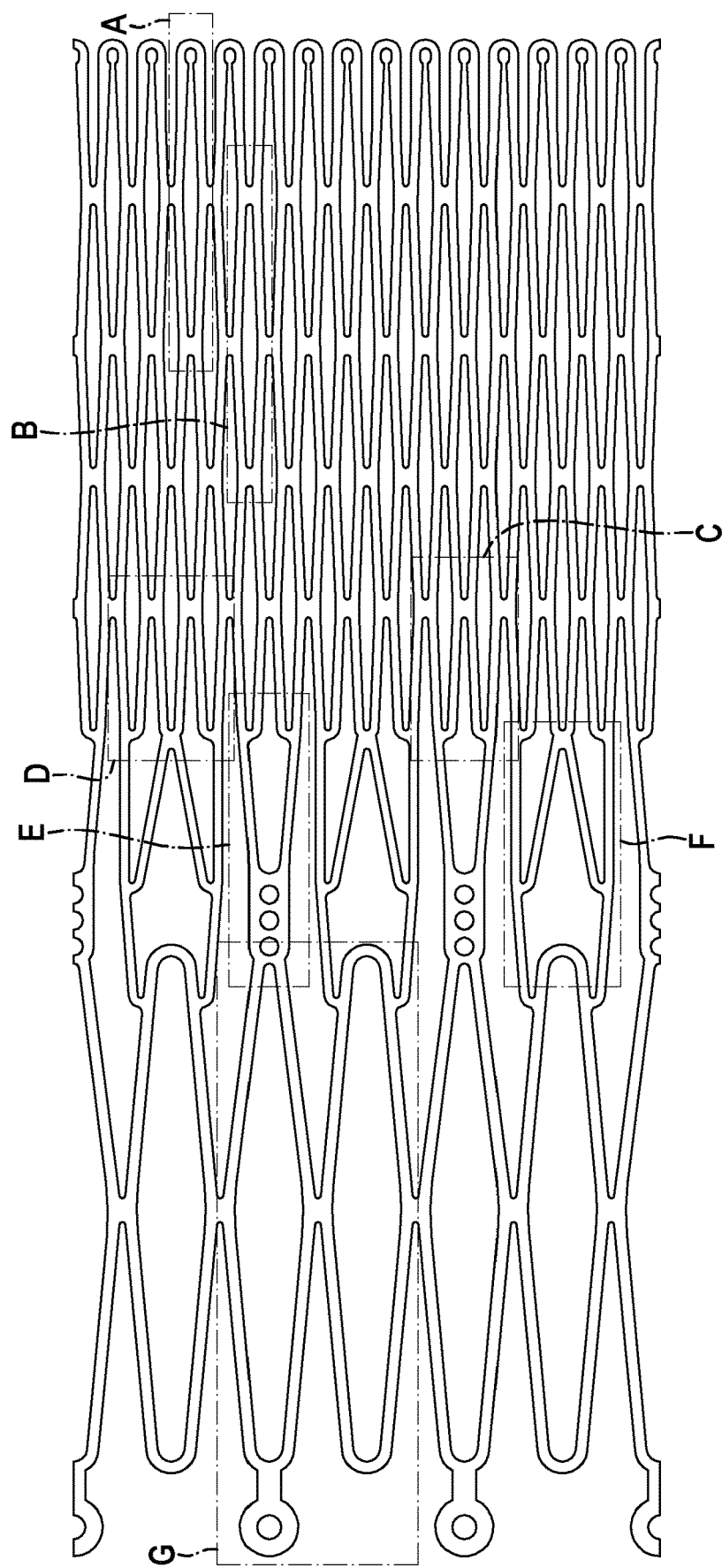
FIG. 14 an overview of a specific mesh structure for stent structure of the prosthetic heart valve of the present invention based on the characteristics of FIG. 1.
Figure 17A:
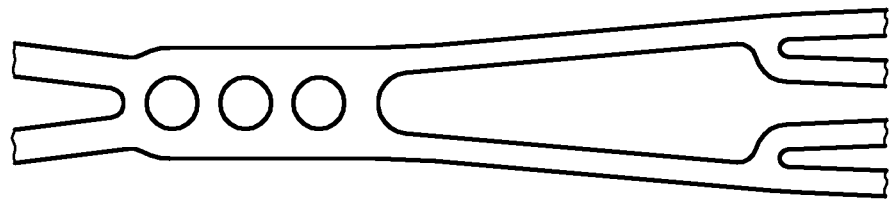
FIGS. 17A-17D detail views of a specific mesh structure for stent structure of the prosthetic heart valve of the present invention based on the characteristics of FIG. 1.
Figure 17B:
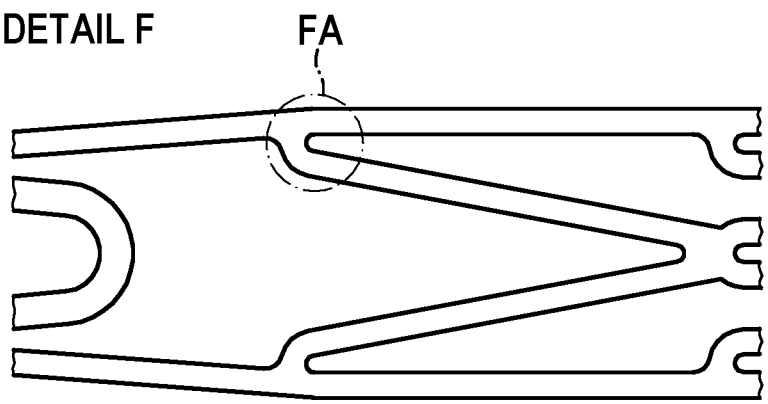
Figure 17C:
Figure 17D:
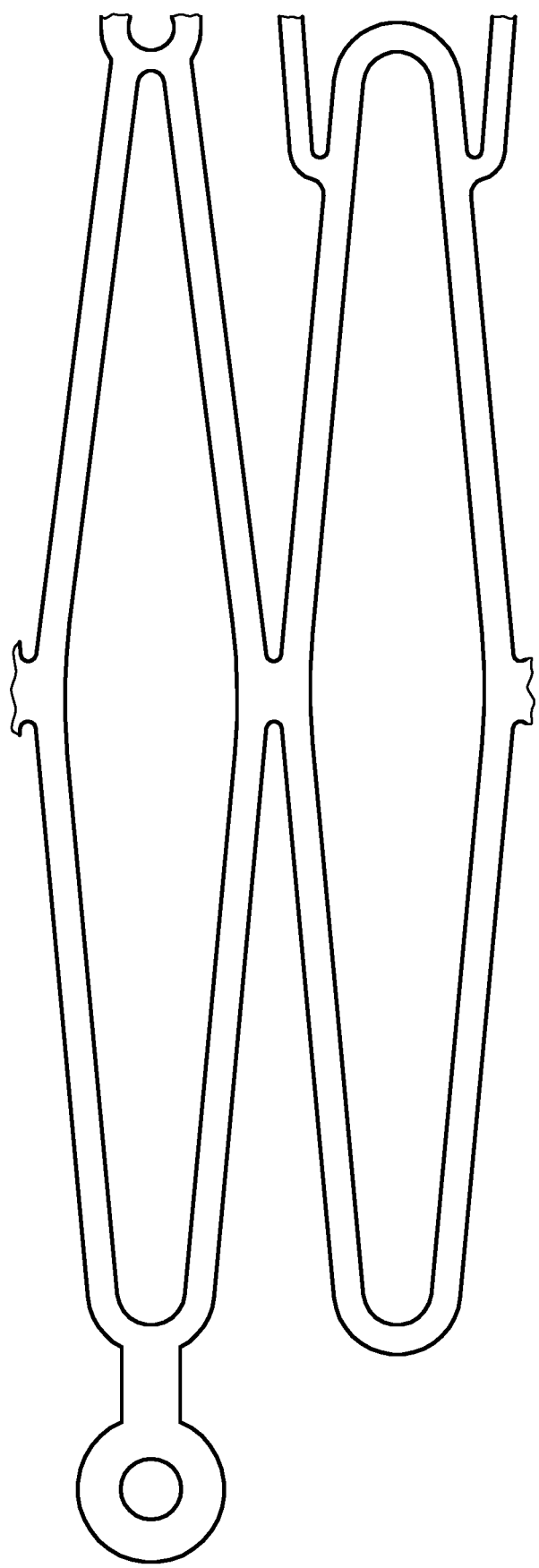

FIG. 14 is a schematic illustration of an overview of a mesh structure for the stent structure of the present invention. By way of example, the pair-wise strut width at positions C01-C12 may be measured three times around the circumference. The wall thickness may be measured, for example, at positions WT01-WT03.

FIGS. 15A-15G: provide various schematic details of a mesh structure for the stent structure of the present invention with some corresponding dimensions [in mm]. DETAIL AA in particular illustrates by way of example the Nutcracker design described in the foregoing of the proximal apical tips in the inflow region (towards the ventricle).

FIGS. 16A-16H: provide various schematic details of a mesh structure for the stent structure of the present invention with some corresponding dimensions [in mm].

FIGS. 17A-17D: provide various schematic details of a mesh structure for the stent structure of the present invention with some corresponding dimensions [in mm]. DETAIL E in particular illustrates by way of example a commissure post in the transition region (transition zone) of the present invention. The upper left region in DETAIL G illustrates an exemplary connector of the present invention in the terminal outflow having a central eyelet.

Referring to the aforesaid disclosure, the present invention further comprises the following consecutively lettered embodiments:

A. A prosthetic heart valve, comprising:
  a stent structure that is configured to expand from a compressed state for transluminal delivery to a natural expanded state, the stent structure comprising a mesh structure that has an essentially tubular shape and that furthermore defines a circumference with contours, wherein the contours define a proximal inlet region (Z1), a distal outlet region (Z3), and an intermediate transition region (Z2), wherein the intermediate transition region (Z2) connects the inlet region (Z1) and outlet region (Z3) to one another, and wherein the mesh structure comprises a plurality of closed cells (1, 2, 3) that in the longitudinal direction of the prosthetic heart valve have varying cell sizes (1, 2, 3) and cell configurations (4b), and thus comprises a plurality of cell patterns (1, 2, 3, 4b) that vary in size between the proximal inlet region (Z1), the distal outlet region (Z3), and the intermediate transition region (Z2), and
  a valve arrangement that is arranged inside a lumen of the stent structure, characterized in that
  the cells in the inlet region (1) are formed and arranged (5) for defining in the stent structure a conical-convex outer shape across the entire circumference of the inlet region (Z1; i.e. a so-called "conical-convex inlet region" or "conical-convex inflow region"), and
  the cells in the outlet region (2) are shaped and arranged for defining in the stent structure a linear cylindrical outer shape across the entire circumference of the outlet region (Z3; i.e. a so-called "linear cylindrical outlet region" or "linear cylindrical outflow region"), and
  two or more cells in the transition region (3) are shaped and arranged for permitting (3) a cell surface area of suitable size for free access to the coronary arteries, further characterized in that
the cells of the inlet region (1), outlet region (2), and transition region (3) are configured differently from one another to always build up, when the stent structure is in the expanded state, a higher maximum radial force in the inlet region (Z1) in direct is comparison to the lower maximum radial force in the outlet region (Z3) and in the transition region (Z2).

B. The prosthetic heart valve according to embodiment A, wherein the valve arrangement comprises a plurality of valve leaflets that are arranged for defining an entry side and an exit side in the prosthetic heart valve.

C. The prosthetic heart valve according to embodiment A or B, wherein the valve arrangement is having two or more valve leaflets, preferably three valve leaflets, and comprises an inner skirt element on the inside of the stent structure, wherein said valve leaflets are sutured or glued at least to the inner skirt element and the inner skirt element is itself sutured or glued to the stent structure.

D. The prosthetic heart valve according to any one of embodiments A to C, wherein the stent structure furthermore comprises an outer skirt element on the outside of the stent structure, wherein the outer skirt element is sutured or glued at least to the stent structure.

E. The prosthetic heart valve according to any one of embodiments A to D, wherein the transition region (Z2) is a conical transition region (Z2) with a cone opposing the conical-convex inflow region (Z1).

F. The prosthetic heart valve according to any one of embodiments A to E, wherein the conical-convex inlet region (Z1), when the stent structure is in the expanded state, defining a first diameter (D1) and the linear cylindrical outlet region (Z3) defining a second diameter (D3), further characterized in that the first diameter (D1) is larger than the second diameter (D3).

G. The prosthetic heart valve according to embodiments E and F, wherein the conical transition region (Z2), when the stent structure is in the expanded state, defines a third diameter (D2) that is smaller than said first diameter (D1) and second diameter (D3).

H. The prosthetic heart valve according to any one of embodiments A to G, further characterized in that the conical-convex inlet region expands proximally towards the inlet (Z1).

I. The prosthetic heart valve according to any one of embodiments A to H, each of the closed cells (1, 2, 3) comprises a plurality of struts (5, 6) connected to one another, and each strut itself comprises a plurality of segments (6a, 6b, 6c) connected to one another, and wherein furthermore a geometry of at least one of the struts and/or of at least one of the segments of the closed cells in the inlet region (Z1) is smaller than a corresponding geometry of a corresponding strut and/or a corresponding segment in the closed cells of the outlet region (Z3).

J. The prosthetic heart valve according to embodiment I, wherein the geometry is a length of a strut and/or of a segment of the strut.

K. The prosthetic heart valve according to embodiment I or J, wherein the geometry is a width of a strut and/or a segment of the strut.

L. The prosthetic heart valve according to any one of embodiments A to K, further characterized in that the outlet region (Z3) at the distal end comprises one or more connector elements (Z4, Detail G), preferably three connector elements.

M. The prosthetic heart valve according to embodiment L, wherein the one or more connector elements (Detail G) are oriented inward toward the outlet center.

N. The prosthetic heart valve according to embodiment L or M, wherein at least one of the connector elements has an eyelet (Detail G).

O. The prosthetic heart valve according to any one of embodiments A to N, further characterized in that the inlet region comprises one or more cell rows.

P. The prosthetic heart valve according to any one of embodiments A to O, wherein the inlet region (Z1) comprises one or more cell rows to define a first band of closed cells that extend about an entirety of the circumference of the inlet region, wherein the closed cells of the first band (1) are spaced equidistant from one another along the circumference, and further wherein the first band is configured to always build up the highest radial force along the circumference when the stent structured is in the expanded state in direct comparison to the radial force of the rest of the stent structure.

Q. The prosthetic heart valve according to any one of embodiments A to P, wherein the inlet region (Z1) comprises one or more cell rows comprising 12, 15, or 18 cells.

R. The prosthetic heart valve according to any one of embodiments Aa to Q, further characterized in that the proximal apical tips of the cells in the inlet region, in direction of the inflow, have a nutcracker shape (7, 8) for fixing sutures of the valve arrangement.

S. The prosthetic heart valve according to any one of embodiments A to R, wherein the outlet region (Z3) comprises one or more cell rows comprising 3, 6, or 9 cells.

T. The prosthetic heart valve according to any one of embodiments A to S, wherein the transition region (Z2) comprises at least one cell row, preferably at least two cell rows, more preferably at least three cell rows.

U. The prosthetic heart valve according to any one of embodiments A to T, further characterized in that, for fixing the valve arrangement, at least one commissure post (4a) is arranged between the inlet region (Z1) and the outlet region (Z3) of the mesh structure in the stent structure.

V. The prosthetic heart valve according to any one of embodiments B to U, wherein the valve leaflets being formed from a material selected from the group consisting of porcine, bovine, equine, or other mammalian pericardial tissue, synthetic material, or polymeric material.

W. The prosthetic heart valve according to any one of embodiments B to V, wherein the valve leaflets being deployable superannularly from the aortic annulus of a patient when the prosthetic heart valve is advanced inside the aortic valve of a patient and the stent structure is in the expanded state.

X. The prosthetic heart valve according to any one of embodiments C to W, wherein the inner skirt is being formed from a material selected from the group consisting of porcine, bovine, equine, or other mammalian pericardial tissue, synthetic material, or polymeric material.

Y. The prosthetic heart valve according to any of embodiments D to X, wherein the outer skirt is being formed from a material selected from the group consisting of porcine, bovine, equine, or other mammalian pericardial tissue, synthetic material, or polymeric material.

Z. The prosthetic heart valve according to any one of embodiments A to Y, wherein the stent structure is being configured for holding the native heart valve of a patient continuously open when in the expanded state.

AA. The prosthetic heart valve according to any one of the embodiments A to Z, wherein the prosthetic heart valve is being configured as a replacement for a native aortic valve.

BB. A method for treating a patient's native heart valve, the method comprising the following steps:
- transporting a prosthetic heart valve according to embodiments 1 to 27 to the native heart valve, the step of transporting the prosthetic heart valve including holding the stent structure in the compressed state inside a delivery device;
- supplying the prosthetic heart valve from the delivery device to the native heart valve, including the stent structure that automatically expands in the direction of its natural state; and,
- aligning the conical-convex inlet region in a desired anatomical position of the native heart valve.

CC. The method according to embodiment BB, wherein the native heart valve is an aortic valve.

DD. The method according to embodiment BB or CC, wherein the desired anatomical position is in the annulus plane.

The invention claimed is:

1. A prosthetic heart valve, comprising:
    a stent structure that is configured to expand from a compressed state for transluminal delivery to a natural expanded state, the stent structure comprising a mesh structure that has an essentially tubular shape and that furthermore defines a circumference with contours, wherein the contours define a proximal inlet region, a distal outlet region, and an intermediate transition region, wherein the intermediate transition region connects the inlet region and outlet region to each another, and wherein the mesh structure comprises a plurality of closed cells that in the longitudinal direction of the prosthetic heart valve have varying cell sizes and cell configurations to define a plurality of cell patterns that vary in size between the proximal inlet region, the distal outlet region, and the intermediate transition region, and
    a valve arrangement that is arranged inside a lumen of the stent structure, wherein:
    the cells in the inlet region are formed and arranged to define a conical-convex outer shape across the entire circumference of the inlet region,
    the cells in the outlet region are shaped and arranged to define a linear cylindrical outer shape across the entire circumference of the outlet region,
    two or more cells in the transition region are shaped and arranged for permitting a cell surface area of suitable size for free access to the coronary arteries, and
    the inlet region comprises a higher number of smaller cells than the outlet region to create, when the stent structure is in the expanded state, a higher maximum radial force in the inlet region in direct comparison to a lower maximum radial force in the outlet region and in the transition region, wherein the transition region has the smallest diameter of the entire stent structure.

2. The prosthetic heart valve according to claim 1, wherein the valve arrangement comprises a plurality of valve leaflets that are arranged for defining an entry side and an exit side in the prosthetic heart valve.

3. The prosthetic heart valve according claim 1, wherein the valve arrangement comprises three valve leaflets, and comprises an inner skirt element on the inside of the stent structure, wherein said valve leaflets are sutured or glued at least to the inner skirt element and the inner skirt element is itself sutured or glued to the stent structure.

4. The prosthetic heart valve according to any one of claim 1, wherein the stent structure furthermore comprises an outer skirt element on the outside of the stent structure, wherein the outer skirt element is sutured or glued at least to the stent structure.

5. The prosthetic heart valve according to claim 1, wherein the conical-convex inlet region expands proximally towards the inlet.

6. The prosthetic heart valve according to claim 1, wherein each of the closed cells comprises a plurality of struts connected to one another, and each strut itself comprises a plurality of segments connected to one another, and wherein a geometry of at least one of the struts and/or of at least one of the segments of the closed cells in the inlet region is smaller than a corresponding geometry of a corresponding strut and/or a corresponding segment in the closed cells of the outlet region.

7. The prosthetic heart valve according to claim 1, wherein the outlet region at the distal end comprises one or more connector elements.

8. The prosthetic heart valve according to claim 7, wherein the one or more connector elements are oriented inward toward the outlet center.

9. The prosthetic heart valve according to claim 7, wherein at least one of the one or more connector elements has an eyelet.

10. The prosthetic heart valve according to claim 1, wherein the inlet region comprises one or more cell rows.

11. The prosthetic heart valve according to claim 1, wherein the outlet region comprises a diameter that prevents circumferential contact sufficient to provide a sealing, anchoring, or aligning function with a vascular wall of the ascending aorta.

12. A prosthetic heart valve, comprising:
    a stent structure that is configured to expand from a compressed state for transluminal delivery to a natural expanded state, the stent structure comprising a mesh structure that has an essentially tubular shape and that furthermore defines a circumference with contours, wherein the contours define a proximal inlet region, a distal outlet region, and an intermediate transition region, wherein the intermediate transition region connects the inlet region and outlet region to each another, and wherein the mesh structure comprises a plurality of closed cells that in the longitudinal direction of the prosthetic heart valve have varying cell sizes and cell configurations to define a plurality of cell patterns that vary in size between the proximal inlet region, the distal outlet region, and the intermediate transition region, and
    a valve arrangement that is arranged inside a lumen of the stent structure, wherein:
    the cells in the inlet region are formed and arranged to define a conical-convex outer shape across the entire circumference of the inlet region,
    the cells in the outlet region are shaped and arranged to define a linear cylindrical outer shape across the entire circumference of the outlet region,
    two or more cells in the transition region are shaped and arranged for permitting a cell surface area of suitable size for free access to the coronary arteries, and
    the cells of the inlet region, outlet region, and transition region are configured differently from one another to create, when the stent structure is in the expanded state, a higher maximum radial force in the inlet region in direct comparison to a lower maximum radial force in the outlet region and in the transition region, wherein the conical-convex inlet region, when the stent structure is in the expanded state, defines a first diameter and the linear cylindrical outlet region defines a second diameter, and the first diameter is larger than the second diameter, wherein the conical transition region, when the stent structure is in the expanded state, defines a third diameter that is smaller than the first diameter and the second diameter.

13. A prosthetic heart valve comprising:
a stent structure configured to expand from a compressed state for transluminal delivery to a natural expanded state, and
a valve arrangement that is arranged inside a lumen of the stent structure,
wherein the stent structure comprises a conical-convex inflow region, a linear cylindrical outflow region and a transition region between the inflow region and outflow region, wherein the transition region connects the inflow region and the outflow region to one another, and wherein,
the stent structure comprises a mesh structure,
   the mesh structure comprises a plurality of closed cells that in a longitudinal direction of the prosthetic heart valve have varying cell sizes and cell configurations, and
wherein each of the closed cells includes a plurality of struts that are connected to one another, and wherein the struts have varying strut widths and strut lengths, and wherein the conical-convex inflow region comprises an atraumatic apical tip element comprising an apical are and two individual thickenings in strut width in a vicinity of the arc, the two individual thickenings being configured to provide a fixed suture node position disposed at apical tips of the cells, wherein the transition region has the smallest diameter of the entire stent structure.

14. The prosthetic heart valve according to claim 13, wherein the strut width varies along the struts such that the width is minimal at two positions along the strut.

15. The prosthetic heart valve according to claim 14, wherein the strut width between the two positions is larger but equal to or smaller than the strut width at a node element that connects two struts of each of the closed cells to one another.

16. The prosthetic heart valve according to claim 13, wherein the strut width varies along the struts such that the width in a center of the struts is smaller than at a node element that connects two struts of each of the closed cells to one another, and wherein each strut has the same length.

17. The prosthetic heart valve according to claim 13, wherein the stent structure comprises one or more connector elements at the distal end of the linear cylindrical outflow region.

* * * * *